(12) United States Patent
Levy et al.

(10) Patent No.: US 9,380,947 B2
(45) Date of Patent: Jul. 5, 2016

(54) METHOD AND SYSTEM FOR MONITORING HEMODYNAMICS

(75) Inventors: Baruch Levy, LeHavim (IL); Shmuel Marcovitch, Kfar-Saba (IL); Eliezer Shusman, RaAnana (IL); David Rotenberg, Natania (IL); Dan Avidor, Tel-Aviv (IL); Yoav Avidor, legal representative, Tel-Aviv (IL)

(73) Assignee: Cheetah Medical, Inc., Wilmington, DE (US)

( * ) Notice: Subject to any disclaimer, the term of this patent is extended or adjusted under 35 U.S.C. 154(b) by 179 days.

(21) Appl. No.: 14/235,101

(22) PCT Filed: Jul. 25, 2012

(86) PCT No.: PCT/IL2012/050271
§ 371 (c)(1),
(2), (4) Date: Jan. 27, 2014

(87) PCT Pub. No.: WO2013/014671
PCT Pub. Date: Jan. 31, 2013

(65) Prior Publication Data
US 2015/0366468 A1 Dec. 24, 2015

Related U.S. Application Data

(60) Provisional application No. 61/511,163, filed on Jul. 25, 2011.

(51) Int. Cl.
*A61B 5/02* (2006.01)
*A61B 5/029* (2006.01)
(Continued)

(52) U.S. Cl.
CPC ......... *A61B 5/02028* (2013.01); *A61B 5/02007* (2013.01); *A61B 5/029* (2013.01);
(Continued)

(58) Field of Classification Search
CPC ...... A61B 8/06; A61B 5/02007; A61B 5/029; A61B 5/11; A61B 5/02028; A61B 5/048; A61B 8/5223; A61B 5/7264; A61B 5/0205; A61B 5/725; A61B 5/7278; A61B 5/026; A61B 5/04017; A61B 5/145; A61B 5/4836; A61B 5/7235; A61B 6/507; G01R 33/4824; G01R 33/5602; G01R 33/56316; G01R 33/56308; G01R 33/5673; A61N 1/08; A61N 1/36514; A61N 1/37; A61N 1/025; A61N 1/36125; A61N 1/3684; A61N 1/3727; A61N 2005/0626; G01S 7/5202; G01S 7/52028; G01S 7/52038; G01S 15/8963; G06F 19/3418; G06F 19/34; H04L 1/0036; H04L 1/0045; H04L 27/00; H04L 27/2271; H04L 27/2273
See application file for complete search history.

(56) References Cited

U.S. PATENT DOCUMENTS 3,340,867 A 9/1967 Kubicek et al.
4,450,527 A 5/1984 Sramek
(Continued)

FOREIGN PATENT DOCUMENTS

CN 1244779 2/2000
CN 101553163 10/2009
(Continued)

OTHER PUBLICATIONS

Translation Dated Feb. 25, 2015 of Notification of Office Action and Search Report Dated Feb. 2, 2015 From the State Intellectual Property Office of the People's Republic of China Re. Application No. 201280044422.8.
(Continued)

*Primary Examiner* — Deborah Malamud

(57) ABSTRACT

A system for monitoring hemodynamics of a subject is disclosed. The system comprises: a signal generating system configured for providing at least an output electric signal and transmitting the output signal to an organ of the subject. The system also comprises a demodulation system configured for receiving an input electrical signal sensed from the organ responsively to the output electric signal, and for modulating the input signal using the output signal to provide an in-phase component and a quadrature component of the input signal. The system also comprises a processing system configured for monitoring the hemodynamics based on the in-phase and the quadrature components.

53 Claims, 12 Drawing Sheets
(5 of 12 Drawing Sheet(s) Filed in Color)

(51) Int. Cl.
| | |
|---|---|
| A61B 5/00 | (2006.01) |
| A61B 5/0402 | (2006.01) |
| A61B 5/053 | (2006.01) |
| A61B 5/024 | (2006.01) |

(52) U.S. Cl.
 CPC .............. *A61B 5/0402* (2013.01); *A61B 5/053* (2013.01); *A61B 5/412* (2013.01); *A61B 5/4818* (2013.01); *A61B 5/7228* (2013.01); *A61B 5/024* (2013.01); *A61B 5/4836* (2013.01); *A61B 5/7239* (2013.01)

(56) References Cited

U.S. PATENT DOCUMENTS

| | | | |
|---|---|---|---|
| 4,852,580 | A | 8/1989 | Wood |
| 4,870,578 | A | 9/1989 | Vysin et al. |
| 4,926,868 | A | 5/1990 | Larsen |
| 4,953,556 | A | 9/1990 | Evans |
| 5,178,154 | A | 1/1993 | Ackmann et al. |
| 5,309,917 | A | 5/1994 | Wang et al. |
| 5,316,004 | A | 5/1994 | Chesney et al. |
| 5,423,326 | A | 6/1995 | Wang et al. |
| 5,469,859 | A | 11/1995 | Tsoglin et al. |
| 5,503,157 | A | 4/1996 | Sramek |
| 5,505,209 | A | 4/1996 | Reining |
| 5,529,072 | A | 6/1996 | Sramek |
| 5,642,734 | A | 7/1997 | Ruben et al. |
| 5,685,316 | A | 11/1997 | Schookin et al. |
| 6,485,431 | B1 | 11/2002 | Campbell |
| 6,496,732 | B1 | 12/2002 | Wallace |
| 6,511,438 | B2 | 1/2003 | Bernstein et al. |
| 2002/0062086 | A1 | 5/2002 | Miele et al. |
| 2002/0193689 | A1 | 12/2002 | Bernstein et al. |
| 2009/0240133 | A1 | 9/2009 | Friedman et al. |
| 2009/0287102 | A1 | 11/2009 | Ward |

FOREIGN PATENT DOCUMENTS

| | | |
|---|---|---|
| WO | WO 2004/028361 | 4/2004 |
| WO | WO 2004/098376 | 11/2004 |
| WO | WO 2006/087696 | 8/2006 |
| WO | WO 2008/036396 | 3/2008 |
| WO | WO 2008/129535 | 10/2008 |
| WO | WO 2009/022330 | 2/2009 |
| WO | WO 2010/032252 | 3/2010 |
| WO | WO 2013/014671 | 1/2013 |

OTHER PUBLICATIONS

Corrected Written Opinion Dated Nov. 14, 2012 From the International Searching Authority Re. Application No. PCT/IL2012/050271.
International Search Report and the Written Opinion Dated Oct. 24, 2012 From the International Searching Authority Re. Application No. PCT/FL2012/050271.
Analog Devices "DC to 50 MHz, Dual I/Q Demodulator and Phase Shifter, AD 8333", Analog Devices, 32P., 2005-2010.
Hccrdt et al. "Noninvasive Cardiac Output Monitoring With Bioreactance as an Alternative to Invasive Instrumentation for Preclinical Drug Evaluation in Beagles", Journal of Pharmacological and Toxicological Methods, 8 P., Epub Ahead of Print, Apr. 2, 2011.
Marque et al. "Comparison Between Flotrac-Vigileo and Bioreactance, A Totally Noninvasive Method for Cardiac Output Monitoring", Critical Care, 13(3): R73-1-R73-6, May 19, 2009.
Raval et al. "Multicenter Evaluation of Noninvasive Cardiac Output Measurement by Bioreactance Technique", Journal of Clinical Monitoring and Computing, 22(2): 113-119, Apr. 2008.
Rich et al. "Evaluation of Noninvasively Measured Cardiac Output in Patients With Pulmonary Hypertension", American Journal of Respiratory and Critical Care Medicine, 183: A6440, 2011, Poster Discussion Session, May 18, 2011. Abstract & Poster.
Rich et al. "Noninvasive Cardiac Output Measurements in Patients With Pulmonary Hypertension", The European Respiratory Journal Express, p. 1-29, Oct. 25, 2012.
Squara et al. "Comparison of Monitoring Performance of Bioreactance Vs. Pulse Contour During Lung Recruitment Maneuvers", Critical Care, 13(4): R125-1-R125-6, Jul. 28, 2009.
Squara et al. "Noninvasive Cardiac Output Monitoring (NICOM): A Clinical Validation", Intensive Care Medicine, 33(7): 1191-1194, Jul. 2007.
International Preliminary Report on Patentability Dated Feb. 6, 2014 From the International Bureau of WIPO Re. Application No. PCT/IL2012/050271.
Notification of Office Action and Search Report Dated Feb. 2, 2015 From the State intellectual Property Office of the People's Republic of China Re. Application No. 201280044422.8.
Supplementary European Search Report and the European Search Opinion Dated Jan. 13, 2015 From the European Patent Office Re. Application No. 12817147.7.
Prevot "Arterial Perfusion Detection Method by Synchronous Detection", Thesis Submitted in Partial Fulfillment of the Requirements for the Degree of Master of Science in Electrical Engineering, Department of Electrical Engineering, College of Engineering, University of South Florida, Graduate Theses and Dissertations, 106 p. 04 Nov. 2005. p. 17-18, Section 3.1.8, p. 43-45, Fig.3.1.
Notification of Office Action and Search Report Dated Oct. 16, 2015 From the State Intellectual Property Office of the People's Republic of China Re. Application No. 201280044422.8 and Its Translation Into English.
Patent Examination Report Dated Feb. 15, 2016 From the Australian Government, IP Australia Re. Application No. 2012288416.

METHOD AND SYSTEM FOR MONITORING HEMODYNAMICS

RELATED APPLICATIONS

This application is a National Phase of PCT Patent Application No. PCT/IL2012/050271 having International filing date of Jul. 25, 2012, which claims the benefit of priority under 35 USC §119(e) of U.S. Provisional Patent Application No. 61/511,163 filed on Jul. 25, 2011. The contents of the above applications are all incorporated by reference as if fully set forth herein in their entirety.

FIELD AND BACKGROUND OF THE INVENTION

The present invention, in some embodiments thereof, relates to the medical field and, more particularly, but not exclusively, to a method and system for monitoring hemodynamics.

Heart diseases are major causes of morbidity and mortality in the modern world. Generally, heart diseases may be caused by (i) a failure in the autonomic nerve system where the impulses from the central nervous system control to the heart muscle fail to provide a regular heart rate and/or (ii) an insufficient strength of the heart muscle itself where even though the patient has a regular heart rate, its force of contraction is insufficient. Either way, the amount of blood or the rate at which the blood is supplied by a diseased heart is abnormal and it is appreciated that an assessment of the state of a patient's circulation is of utmost importance.

The simplest measurements, such as heart rate and blood pressure, may be adequate for many patients, but if there is a cardiovascular abnormality then more detailed measurements are needed.

Cardiac output (CO) is the volume of blood pumped by the heart during a time interval, which is typically taken to be a minute. Cardiac output is the product of heart rate (HR) and the amount of blood which is pumped with each heartbeat, also known as the stroke volume (SV). For example, the stroke volume at rest in the standing position averages between 60 and 80 ml of blood in most adults. Thus, at a resting heart rate of 80 beats per minute the resting cardiac output varies between 4.8 and 6.4 L per min.

Several methods of measuring cardiac output are presently known.

One such method employs transesophageal echocardiography (TOE) which provides diagnosis and monitoring of a variety of structural and functional abnormalities of the heart. TOE is used to derive cardiac output from measurement of blood flow velocity by recording the Doppler shift of ultrasound reflected from the red blood cells. The time velocity integral, which is the integral of instantaneous blood flow velocities during one cardiac cycle, is obtained for the blood flow in a specific site (e.g., the left ventricular outflow tract). The time velocity integral is multiplied by the cross-sectional area and the heart rate to give cardiac output.

U.S. Pat. No. 6,485,431 discloses a technique in which the arterial pressure, measured by a pressure cuff or a pressure tonometer, is used for calculating the mean arterial pressure and the time constant of the arterial system in diastole. The compliance of the arterial system is then determined from a table and used for calculating the cardiac output as the product of the mean arterial pressure and compliance divided by a time constant.

An additional method of measuring cardiac output is known as thermodilution. This method is based on a principle in which the cardiac output can be estimated from the dilution of a bolus of saline being at a different temperature from the blood. The thermodilution involves an insertion of a fine catheter into a vein, through the heart and into the pulmonary artery. A thermistor, mounted on the tip of the catheter senses the temperature in the pulmonary artery. A bolus of saline (about 5 ml. in volume) is injected rapidly through an opening in the catheter, located in or near to the right atrium of the heart. The saline mixes with the blood in the heart and temporarily depresses the temperature in the right atrium. Two temperatures are measured simultaneously: the blood temperature is measured by the thermistor sensor on the catheter and the temperature of the saline to be injected is typically measured by means of a platinum temperature sensor. The cardiac output is inversely related to the area under the curve of temperature depression.

A non-invasive method, known as thoracic electrical bioimpedance, was first disclosed in U.S. Pat. No. 3,340,867 and has recently begun to attract medical and industrial attention (see, e.g., U.S. Pat. Nos. 3,340,867, 4,450,527, 4,852,580, 4,870,578, 4,953,556, 5,178,154, 5,309,917, 5,316,004, 5,505,209, 5,529,072, 5,503,157, 5,469,859, 5,423,326, 5,685,316, 6,485,431, 6,496,732 and 6,511,438; U.S. Patent Application No. 20020193689]. The thoracic electrical bioimpedance method has the advantages of providing continuous cardiac output measurement at no risk to the patient.

Various methods employing bioimpedance are found in: International Publication Nos. WO2004098376, WO2006087696, WO2008129535, WO2009022330 and WO2010032252 all assigned to the common assignee of the present invention and fully incorporated herein by reference.

SUMMARY OF THE INVENTION

According to an aspect of some embodiments of the present invention there is provided a system for monitoring hemodynamics of a subject. The system comprises: a signal generating system configured for providing at least an output electric signal and transmitting the output signal to an organ of the subject. The system also comprises a demodulation system configured for receiving an input electrical signal sensed from the organ responsively to the output electric signal, and for modulating the input signal using the output signal to provide an in-phase component and a quadrature component of the input signal. The system also comprises a processing system configured for monitoring the hemodynamics based on the in-phase and the quadrature components.

According to an aspect of some embodiments of the present invention there is provided a method of monitoring hemodynamics of a subject. The method comprises generating at least an output electric signal, and transmitting the output signal to an organ of the subject. The method further comprises sensing an input electrical signal from the organ responsively to the output electric signal, and modulating the input signal using the output signal to provide an in-phase component and a quadrature component of the input signal. The method further comprises monitoring the hemodynamics based on the in-phase and the quadrature components.

According to some embodiments of the invention the processing system and/or method combines the in-phase component with the quadrature component thereby to generate a hybrid signal, wherein the monitoring is based at least in part on the hybrid signal.

According to some embodiments of the invention the signal generating system and/or method provides a first output electric signal and a second output electric signal, and transmits each of the output signals to a separate part of the organ.

According to some embodiments of the present invention the demodulation system and/or method receives an input electrical signal sensed from each part of the organ responsively to a respective output electric signal, and modulates the signals to provide an in-phase component and a quadrature component of each of the input signals.

According to some embodiments of the invention the processing system and/or method combines, for each input signal, a respective in-phase component with a respective quadrature component thereby to generate a hybrid signal corresponding to the input signal. According to some embodiments of the present invention the monitoring is based at least in part on the hybrid signals.

According to some embodiments of the invention the processing system and/or method combines the hybrid signals, thereby to provide a combined hybrid signal, and wherein the monitoring is based at least in part on the combined hybrid signals.

According to some embodiments of the invention the processing system and/or method combines an in-phase component of a first input signal with an in-phase component of a second input signal to provide a combined in-phase signal. According to some embodiments of the invention the monitoring is based at least in part on the combined in-phase signal.

According to some embodiments of the invention the processing system and/or method combines a quadrature component of a first input signal with a quadrature component of a second input signal to provide a combined quadrature signal. According to some embodiments of the invention the monitoring is based at least in part on the combined quadrature signal.

According to some embodiments of the invention the processing system and/or method calculates, for each input signal, a phase component, an amplitude component, and a phase-amplitude hybrid signal defined as a combination of the phase component with the amplitude component. According to some embodiments of the invention the monitoring is based at least in part on this combination.

According to some embodiments of the invention the processing system and/or method combines a phase-amplitude hybrid signal corresponding to the first input signal with a phase-amplitude hybrid signal corresponding to the second input signal, thereby to provide a combined phase-amplitude hybrid signal. According to some embodiments of the invention the monitoring is based at least in part on the combined phase-amplitude hybrid signal.

According to an aspect of some embodiments of the present invention there is provided a system for monitoring hemodynamics of a subject. The system comprises a signal generating system configured for providing a first output electric signal and a second output electric signal, and for transmitting each of output signals to a separate part of an organ of the subject. The system further comprises a processing system configured for receiving an input electrical signal sensed from each part of the organ responsively to a respective output electric signal, and for monitoring the hemodynamics based on input electrical signals.

According to an aspect of some embodiments of the present invention there is provided a method for monitoring hemodynamics of a subject. The method comprises: generating a first output electric signal and a second output electric, and transmitting each of the output signals to a separate part of an organ of the subject. The method further comprises sensing an input electrical signal from each part of the organ responsively to a respective output electric signal, and monitoring the hemodynamics based on the input electrical signals.

According to some embodiments of the invention the system and/or method combines the input signals to provide a combined signal, wherein the monitoring is based at least in part on the combined signal.

According to some embodiments of the invention any of the above signal combinations is the combination is a linear combination.

According to some embodiments of the invention any of the above signal combinations is a non-linear combination.

According to some embodiments of the invention the processing system and/or method assesses, based on the combined hybrid signal and/or the combined phase-amplitude hybrid signal and/or the combined signal, at least one property selected from the group consisting of stroke volume (SV), cardiac output (CO), ventricular ejection time (VET), cardiac index (CI), thoracic fluid content (TFC), total peripheral resistance index (TPRI), blood vessel compliance.

According to some embodiments of the invention the processing system and/or method estimates exercise capacity of the subject based on the combined hybrid signal and/or the combined phase-amplitude hybrid signal and/or the combined signal.

According to some embodiments of the invention the processing system and/or method identifies sleep apnea events based on the combined hybrid signal and/or the combined phase-amplitude hybrid signal and/or the combined signal.

According to some embodiments of the invention the processing system and/or method assesses the likelihood that the subject develops sepsis based on the combined hybrid signal and/or the combined phase-amplitude hybrid signal and/or the combined signal.

According to some embodiments of the invention the processing system and/or method predicts onset of electromechanical dissociation based on the combined hybrid signal and/or the combined phase-amplitude hybrid signal and/or the combined signal.

According to some embodiments of the invention the processing system and/or method assesses blood hematocrit based on the combined hybrid signal and/or the combined phase-amplitude hybrid signal and/or the combined signal.

According to some embodiments of the invention the first and the second output electric signals are dependent electrical signals.

According to some embodiments of the invention the first and the second output electric signals are independent electrical signals.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic block diagram illustrating a system suitable for monitoring hemodynamics of a subject, according to some embodiments of the present invention;

FIG. 2 is a schematic block diagram illustrating the system, according to other embodiments of the present invention;

FIG. 3 is a is a schematic block diagram illustrating a system which is a combination of the system illustrated in FIG. 1 and the system illustrated in FIG. 2, according to some embodiments of the present invention;

FIG. 4 is a schematic illustration of an operational principle of a demodulation system according to some embodiments of the present invention;

FIGS. 5A and 5B are schematic block diagrams of a demodulation system (FIG. 5A) and a processing system (FIG. 5B) according to some embodiments of the present invention;

FIGS. 6A and 6B show representative examples of a dynamically varying frequency bounds, according to some embodiments of the present invention;

FIG. 6C shows a dynamically varying band pass filter (BPF), according to some embodiments of the present invention;

FIG. 7 is a schematic illustration of a typical morphology of a single beat of a signal and its first derivative, as a function of the time, according to some embodiments of the present invention;

FIG. 8 is a schematic illustration of a prototype system built according to some embodiments of the present invention;

FIG. 9A shows the left ventricle volume signal in ml (blue) as derived by a 3-Fr Micromanometer secured with a purse string suture, as a function of time, synchronized with the ECG signal (black);

FIG. 9B shows a signal $S_{CT}(t)$ obtained according to some embodiments of the present invention (red) synchronized with the ECG signal (black);

Figure 10:
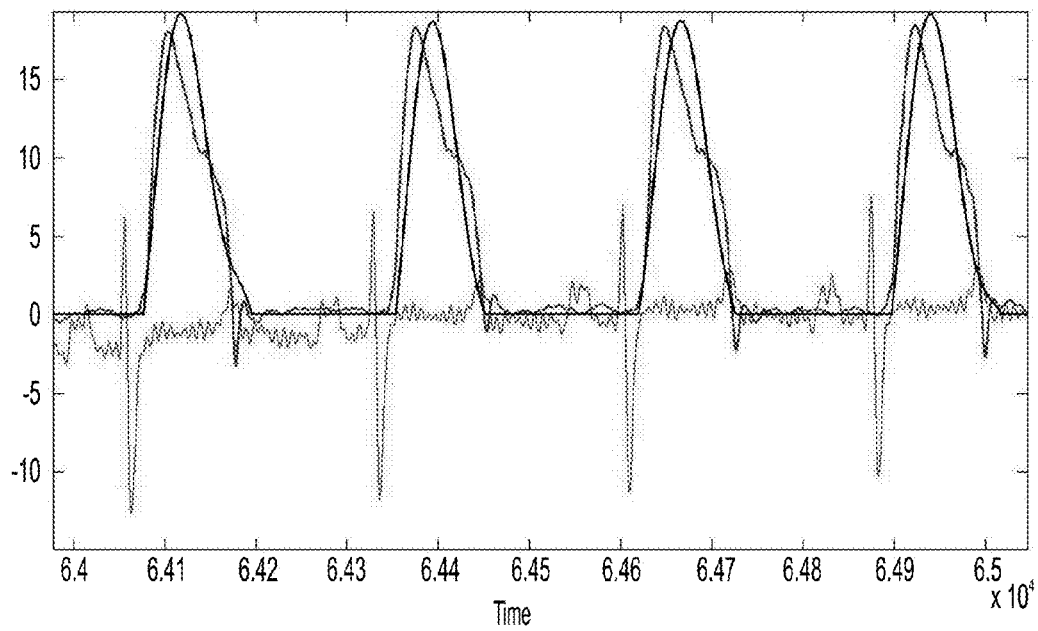
Figure 11:
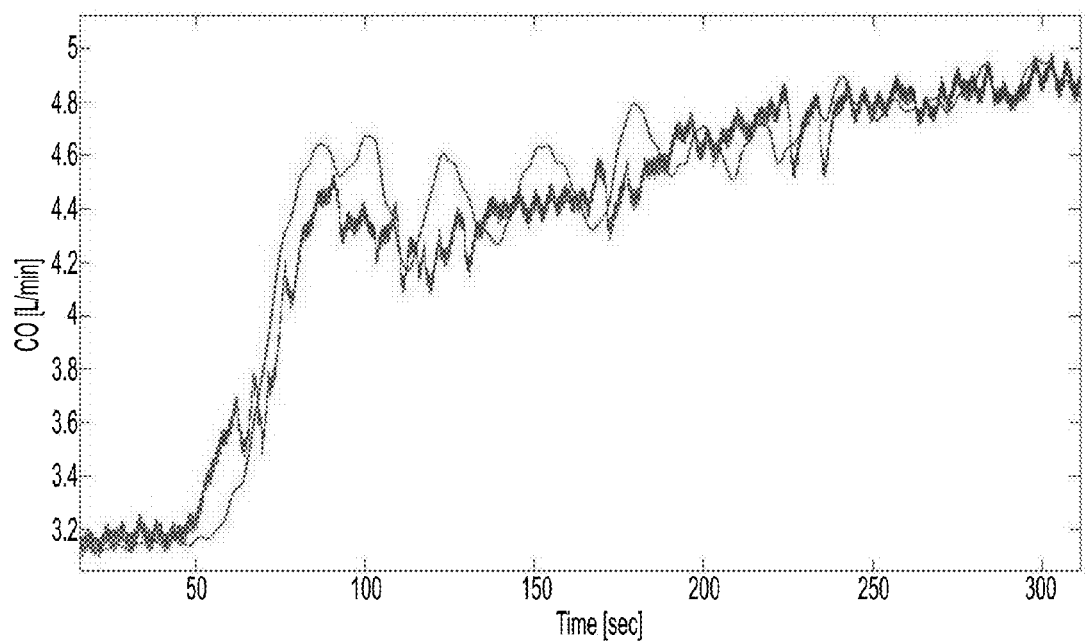
Figure 12A:
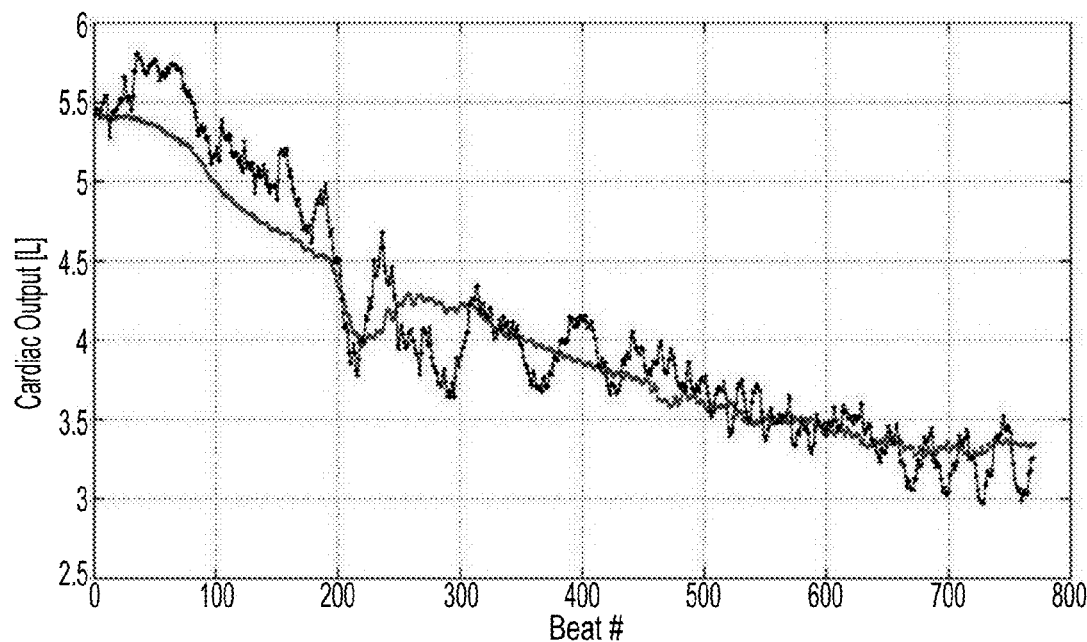
Figure 12B:
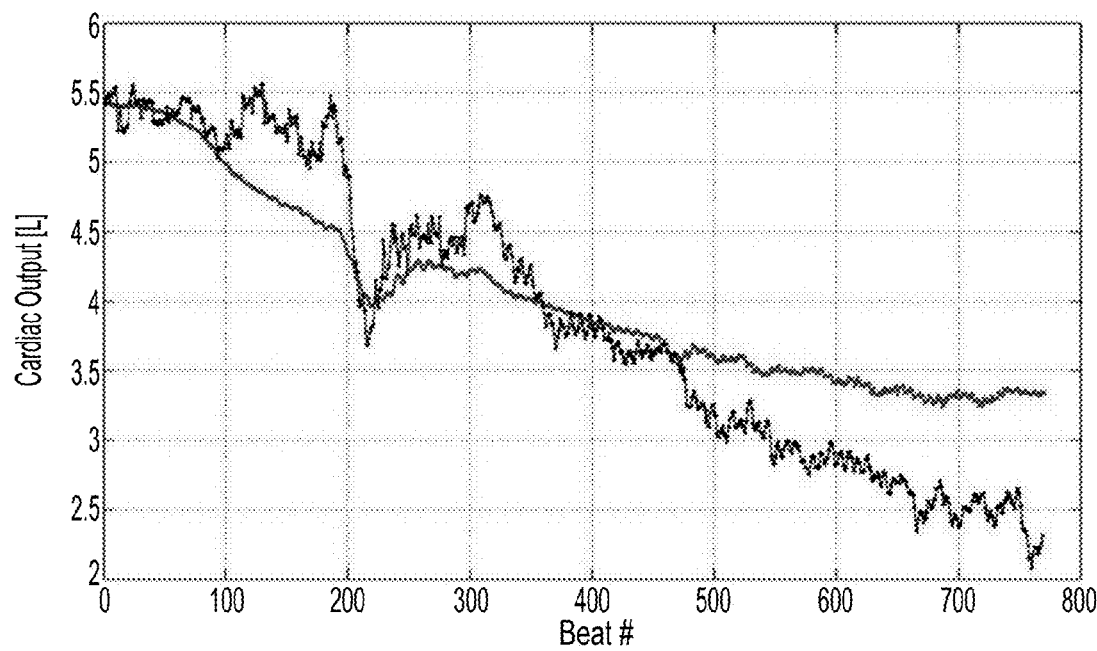
Figure 13A:
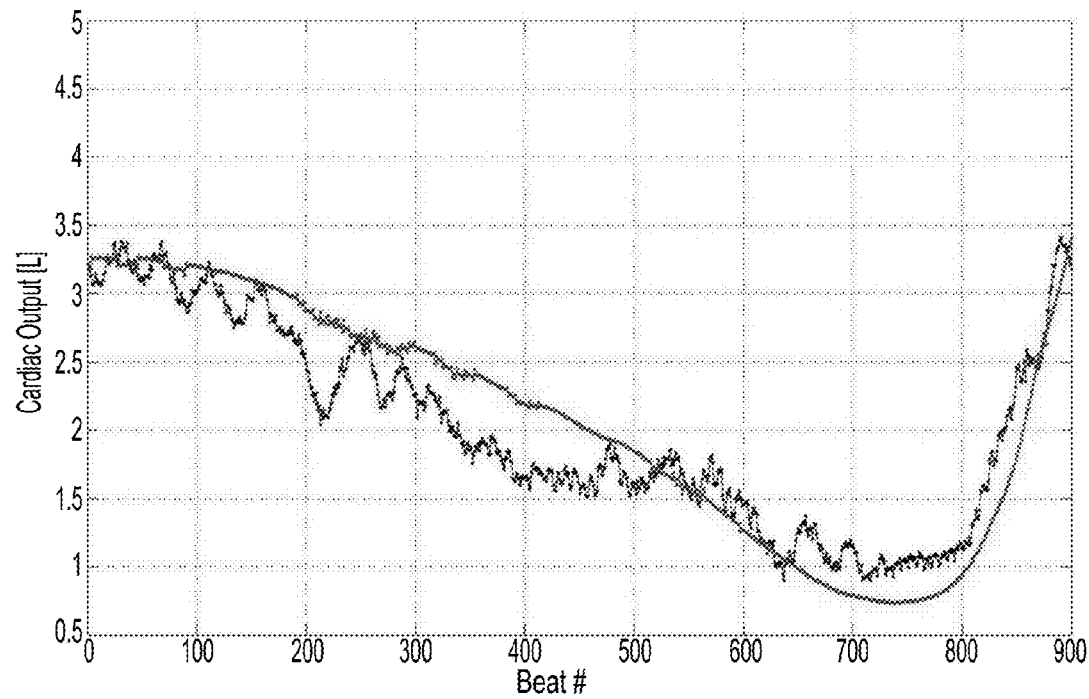
Figure 13B:
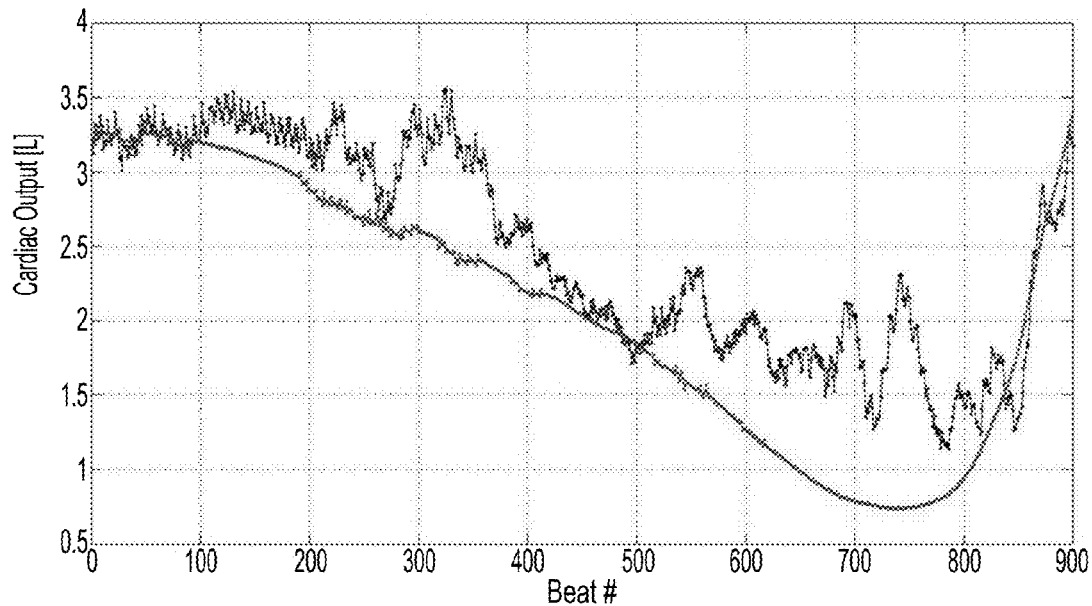
Figure 14:
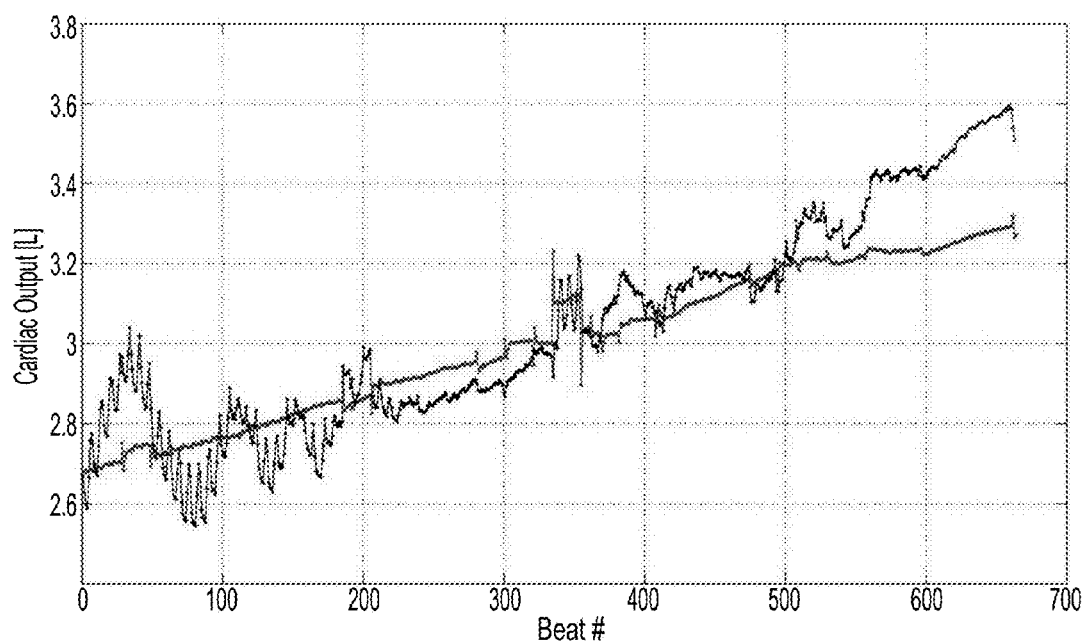

FIG. 10 shows a left ventricle flow signal as derived by an ultrasonic flow probe around the ascending aorta (blue), and a $dS_{CT}(t)$ signal obtained according to some embodiments of the present invention (black);

FIG. 11 shows mean cardiac output as derived by an aortic ultrasonic flow probe (blue), and mean cardiac output derived by a $dS_{CT}(t)$ signal obtained according to some embodiments of the present invention (red) during infusion of Dobutamine;

FIG. 12A shows mean cardiac output as derived by an aortic ultrasonic flow probe (blue), and mean cardiac output derived by a $dS_{CL}(t)$ signal obtained according to some embodiments of the present invention (black), after infusion of Dobutamine;

FIG. 12B shows mean cardiac output as derived by an aortic ultrasonic flow probe as a function of the number of heart beat (blue), and mean cardiac output derived by a $dS_{CR}(t)$ signal obtained according to some embodiments of the present invention (black);

FIG. 13A shows mean cardiac output derived by an aortic ultrasonic flow probe (blue), and mean cardiac output derived by a $dS_{CR}(t)$ signal obtained according to some embodiments of the present invention (black) during progression of Severe Edema;

FIG. 13B shows mean cardiac output derived by an aortic ultrasonic flow probe (blue), and mean cardiac output derived by a $dS_{CL}(t)$ signal obtained according to some embodiments of the present invention (black); and FIG. 14 shows mean cardiac output as derived by an aortic ultrasonic flow probe (blue), and mean cardiac output derived by a $dS_{PT}(t)$ signal obtained according to some embodiments of the present invention (black) during infusion of 500 cc fluid bolus.

DESCRIPTION OF SPECIFIC EMBODIMENTS OF THE INVENTION

The present invention, in some embodiments thereof, relates to the medical field and, more particularly, but not exclusively, to a method and system for monitoring hemodynamics.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present inventors observed that the components of a decomposition of signals can be used to assess the hemodynamic state of a subject, wherein different components are complementary to each other in terms of the information they carry. The present inventors also observed that signals obtained from different parts of the same section of the vasculature are also complementary to each other. The present Inventors devised a technique which utilizes one or both the above observations for the purpose of monitoring hemodynamics of a subject.

Figure 1:
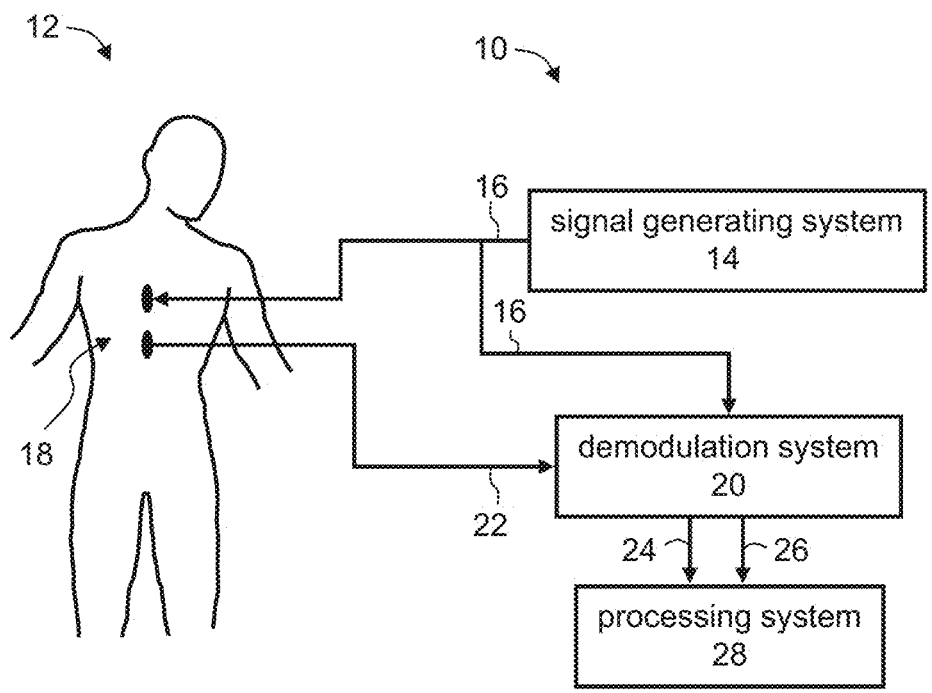

Referring now to the drawings, FIG. 1 is a schematic block diagram illustrating a system 10 suitable for monitoring hemodynamics of a subject 12, according to some embodiments of the present invention. System 10 typically comprises a signal generating system 14 which preferably provides one or more output electric signals 16 and transmits signal 16 to an organ 18 of subject 12. Signal(s) 16 can be transmitted via a medical lead as known in the art.

For clarity of presentation, medical leads are designated herein by the reference signs of the signals they carry.

Organ 18 can be any part of a body of human or animal. Preferably, organ 18 is external organ so that the transmission of signals can be done non-invasively. Representative example of organ 18 include, without limitation, a chest, a hip, a thigh, a neck, a head, an arm, a forearm, an abdomen, a back, a gluteus, a leg and a foot. In some embodiments of the present invention organ 18 is a chest.

In some embodiments of the present invention system 10 comprises a demodulation system 20 configured for receiving an input electrical signal 22 sensed from organ 18 responsively to output signal 16, and for modulating input signal 22 using output signal 16 to provide an in-phase component 24 and a quadrature component 26 of input signal 22. System 10 can further comprise a processing system 28 which, in some embodiments, is configured for monitoring the hemodynamics based on in-phase component 24 and quadrature component 26.

Figure 2:
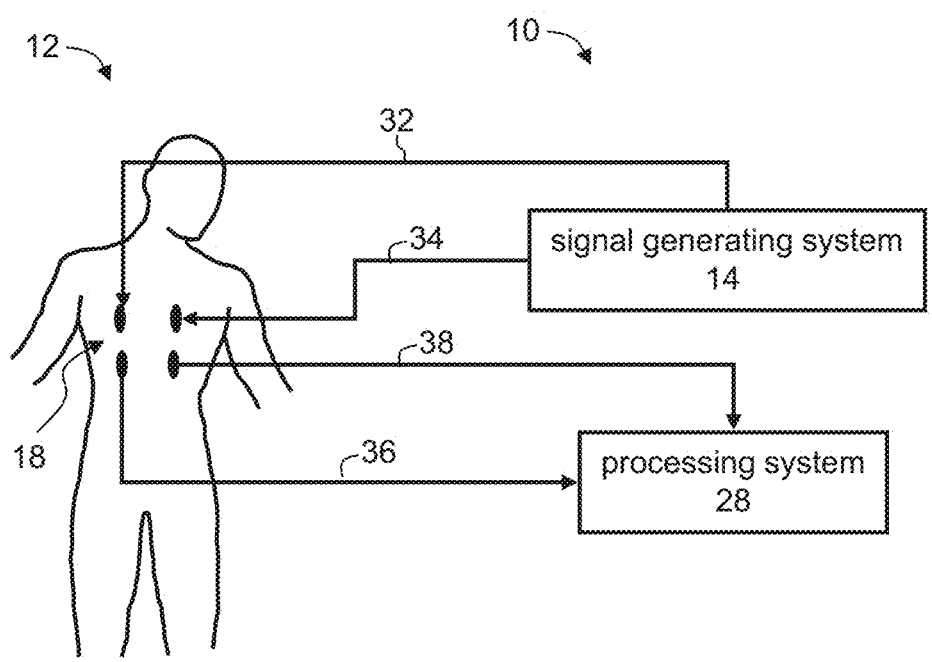

FIG. 2 is a schematic block diagram illustrating system 10, according to other embodiments of the present invention. In the embodiments illustrated in FIG. 2, signal generating system 14 provides two signals, referred to herein as first output electric signal 32 and a second output electric signal 34, and transmits them to separate parts of organ of 18. For example, signal 32 can be transmitted to the left side of organ 18 and signal 34 can be transmitted to the right side of organ 18. In some embodiments of the present invention signals 32 and 34 are dependent signals. Alternatively, signals 32 and 34 can be independent signals.

As used herein, "dependent signals" means signals which are synchronized in at least one, more preferably at least two, more preferably any of: their frequency, phase and amplitude.

As used herein, "independent signals" means signals which are not synchronized in at least one, more preferably at least two, more preferably any of: their frequency, phase and amplitude.

Also contemplated are embodiments in which signal generating system 14 provides more than two (depended or independent) signals.

In the embodiments illustrated in FIG. 2, processing system 28 receives first input electrical signal 36 sensed from the first part of organ 18 (the right side in the above example) responsively to first output signal 32, and a second input electrical signal 38 sensed from the second first part of organ 18 (the left side, in the above example) responsively to second output signal 34. Processing system 28 preferably monitors the hemodynamics based on input signals 36 and 38.

Figure 3:
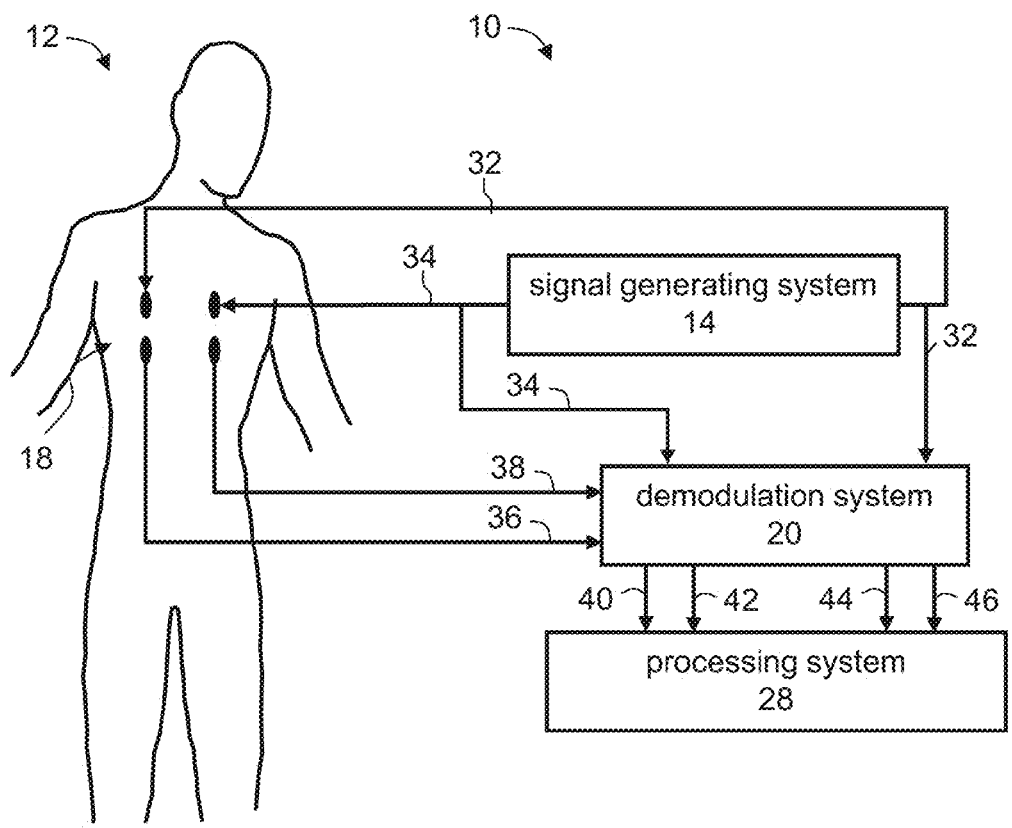

In various exemplary embodiments of the invention the embodiment illustrated in FIG. 1 are combined with the embodiments illustrated in FIG. 2. A representative example of such combination is illustrated in FIG. 3. In the present embodiment, generating system 14 provides two or more output signals, preferably, but not necessarily independent signals and transmits them to separate parts of organ of 18. In the schematic illustration of FIG. 3 which is not to be considered as limiting, generating system 14 provides two signals 32 and 34, and transmits them to the right and left sides of organ 18, respectively.

In some embodiments of the present invention demodulation system 20 receives an input electrical signal sensed from each part of organ 18 responsively to the respective output signal. For example, demodulation system 20 can receive first input signal 36 sensed from the first part of organ 18 responsively to first output signal 32, and second input signal 38 sensed from the second first part of organ 18 responsively to second output signal 34. Demodulation system 20 optionally and preferably modulates all input signals using the input signals to provide, for each input signal, an in-phase component and a quadrature component. Thus, demodulation system 20 preferably provides 2N signals, where N is the number of the received input signals.

In the above example in which demodulation system 20 receives input signals 36 and 38, the output of system 20 is a first in-phase component 40 and a first quadrature component 42 both being demodulations of first input signal 36, and a second in-phase component 44 and a second quadrature component 46 both being demodulations of second input signal 38.

A more detailed description of system 10 as delineated hereinabove and in accordance with some embodiments of the present invention will now be provided.

The signals provided by generating system 14 are preferable alternate current (AC) signals which can be at any frequency. It was found by the present inventors that radiofrequency signals are useful, but it is not intended to limit the scope of the present invention to any particular frequency. Specifically, the frequency of the transmitted signals can be below the radiofrequency range, within the radiofrequency range or above the radiofrequency range. A representative frequency range suitable for the present embodiments include, without limitation, from 20 KHz to 800 KHz, e.g., about 75 KHz. Current, generated by the signal generating system of the present embodiments, flows across the organ and causes a voltage drop due to the impedance of the body. The input radiofrequency signals are typically, but not obligatorily, relate to the impedance of an organ of the subject. In various exemplary embodiments of the invention the parameters (e.g., frequency, amplitude, and phase) of the output signal(s) is selected such that the input signal is indicative of the impedance of organ 18. A typical pick to pick amplitude of the signal is, without limitation, below 600 mv.

Without loss of generality, the input signals are referred to below as "impedance", but it should be understood that a more detailed reference to impedance is not to be interpreted as limiting the scope of the invention in any way, and that the signal be expressed as other measurable electrical quantities, including, without limitation, voltage, current, resistance, reactance, and any combination thereof.

It is recognized that an impedance signal can be expressed as a complex number that satisfies any of the following equations:

$$Z_P = |Z| \exp(j \times \phi_Z) \quad \text{(EQ. 1)}$$

and $$Z_C = Z_r + jZ_i \quad \text{(EQ. 2)}$$

where, $Z_P$ denotes a Polar representation and $Z_C$ denotes a Cartesian representation, and where $|Z|$ is the absolute amplitude of the impedance, $\phi_Z$ is the phase of impedance, $Z_r$ is the real component of the impedance, $Z_i$ is the imaginary component of the impedance, and j is a pure imaginary number satisfying $j^2 = -1$.

The relation between the components ($|Z|$, $\phi_Z$) and ($Z_r$, $Z_i$) is given by:

$$Z_r = |Z|\cos(\phi_Z); Z_r = |Z|\sin(\phi_Z). \quad \text{(EQ. 3)}$$

and $$|Z| = \text{sqrt}(Z_r^2 + Z_i^2); \phi_Z = \arctan(Z_i/Z_r) \quad \text{(EQ. 4)}$$

The polar components $|Z|$ and $\phi_Z$ can be detected using a Amplitude Modulation (AM) envelope detector, and a Phase Modulation (PM) detector, respectively, as disclosed for example, in WO2010032252 supra.

Figure 4:
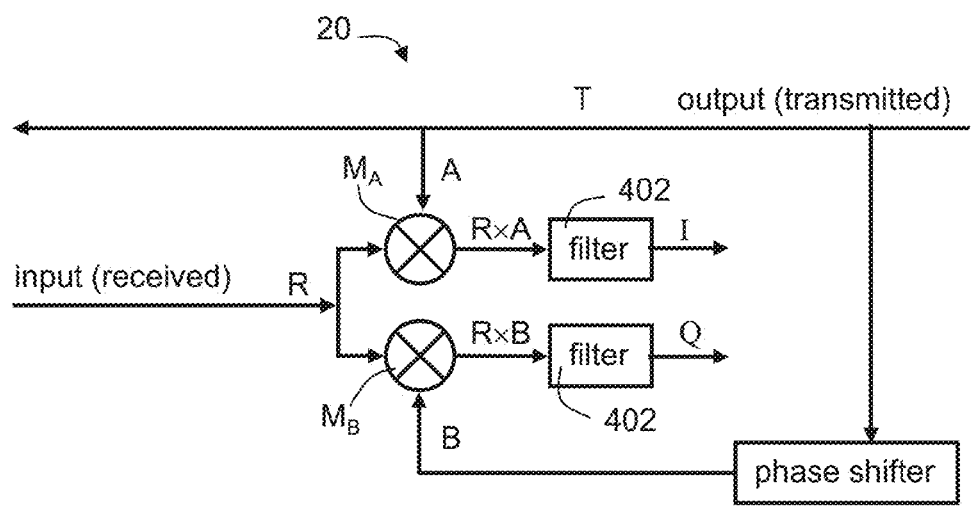

It was found by the present inventors that it is advantage to directly extract from the signal the Cartesian components using quadrature demodulation, which preferably performed by demodulation system 20 for any input signal S received thereby. A preferred operational principle of demodulation system 20 is schematically illustrated in FIG. 4.

In any signal manipulation described herein, the signal and its components are to be understood as varying as function of the time.

Received input signal R is multiplied, in parallel, by (i) a signal A which is in-phase with the transmitted output signal, and (ii) a signal B which is phase-shifted, typically using a phase-shifter 404, relative to the corresponding transmitted output signal T. This procedure provides two multiplication signals, R×A and R×B, respectively. The multiplication signals can be obtained using signal multipliers $M_A$ and $M_B$. The multiplication signals R×A and R×B, are then filtered using low pass filters 402. In some embodiments of the present invention multiplication signals R×A and R×B are also using a high pass filter. This can be achieved, for example, by adding a high pass filter immediately before or immediately after filters 402, or by making filters 402 band pass filters.

A typical cutoff frequency for the low pass filters is, without limitation from about 5 Hz to about 20 Hz or from about 5 Hz to about 15 Hz or from about 8 Hz to about 12 Hz, e.g., a cutoff frequency of about 9 Hz or less. A typical cutoff frequency for the high pass filters LPF is, without limitation from about 0.5 Hz to about 1.5 Hz, or from about 0.6 Hz to about 1.4 Hz or from about 0.7 Hz to about 1.3 Hz, e.g., a cutoff frequency of 0.8 Hz. In various exemplary embodiments of the invention the multiplication signals R×A and R×B are filtered by a dynamically adaptive filter, as further detailed hereinbelow. The dynamically adaptive filter can be in addition to one or both of filters 402. Alternatively, one or both of filters 402, can be replaced by the dynamically adaptive filter.

The filtered signal obtained from R×A is referred to as the in-phase component I of the input signal R and the filtered signal obtained from R×B is referred to as the quadrature component Q of the input signal R.

Typically, the phase shifter generates a phase shift of $\pi/2$, so that B is $\pi/2$ shifted relative to T. However, this need not necessarily be the case since in some embodiments of the present invention phase shifter generates a phase shift which is other than $\pi/2$.

Thus, as used herein, "quadrature component" refers to any signal which is a result of the low-pass filtered multiplication between a received input signal R and a signal B which is phase-shifted with respect to the corresponding output signal T, wherein the phase-shift $\Delta\phi$ of B relative to T is other zero.

In some embodiments of the present invention $\Delta\phi$ is about $\pi/2$.

The demodulation performed by system 20 can be using any known circuitry capable of performing quadrature demodulation. The circuitry can be digital or analog, as desired. In some embodiments of the present invention the circuitry is analog. Suitable analog circuitry is marked under catalog No. AD8333 of Analog Devices Analog Devices, Inc., Norwood, Mass.

Figure 5A:
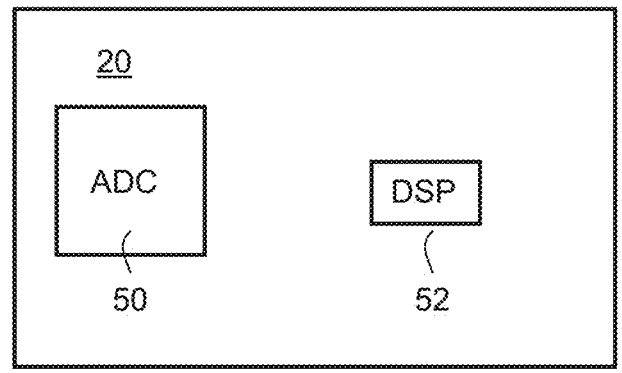

In some embodiments of the present invention, demodulation system 20 performs the processing in a digital manner. In these embodiments, demodulation system 20 comprises an analog to digital converter and a digital data processor or/and a digital signal processor or/and a field-programmable gate array. A representative example of a system 20 having an analog to digital converter (ADC) 50 and a digital signal processor (DSP) 52 is illustrated in FIG. 5A. Analog signals are received by ADC 50 are digitized according to a predetermined sampling rate and transmitted as vectors of discrete data to data DSP 52. A typical sample rate is, without limitation, from about 200 KHz to about 1.5 MHz. DSP 52 receives the input signal R and the transmitted signal T, and calculate the I and Q signals as further detailed hereinabove except that it is performed digitally. Thus, referring again to FIG. 4, when demodulation system 20 performs the processing in a digital manner, phase shifter 404, signal multipliers $M_A$ and $M_B$, and filters 402 can each independently be digital elements.

Processing system 28 serves for providing the monitoring information carried by the input signals. System 28 receives the signals from system 20 (FIGS. 1 and 3) or directly from the organ (FIG. 2), processes the signals and generates an output pertaining to the processed signals. Preferably, the output is a graphical output, which is transmitted to a computer readable medium, such as a display card, a network card or memory medium of a computer. From the computer readable medium the output can be read by a local or remote computer and displayed, e.g., on a display device.

Optionally and preferably processing system 28 performs the processing in a digital manner. In these embodiments, processing system 28 can comprise an analog to digital converter and a digital data processor or a digital signal processor. When demodulation system 20 is digital, it is not required for processing system 28 to include an analog to digital converter since in these embodiments processing system 28 receives digital signals from demodulation system 20.

Figure 5B:
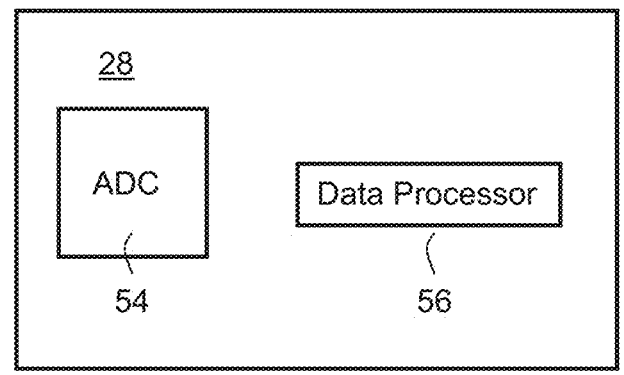

A representative example of a system 28 having an analog to digital converter (ADC) 54 and a data processor 56 is illustrated in FIG. 5B. This embodiment is useful when the output of demodulation system 20 (e.g., after filters 402) includes analog signals. The analog signals are received by ADC 54, digitized according to a predetermined sampling rate and transmitted as vectors of discrete data to data processor 56. A typical sample rate is, without limitation, from about 200 Hz to about 800 Hz.

Data processor 56 can be a general purpose computer or dedicated circuitry. Computer programs implementing the processing technique of the present embodiments can commonly be distributed to users on a distribution medium such as, but not limited to, a floppy disk, CD-ROM or flash memory. From the distribution medium, the computer programs can be copied to a hard disk or a similar intermediate storage medium. Alternatively, the computer program can be distributed as a data stream downloadable, e.g., from an http or ftp internet site, in which case the computer program is copied to the computer directly from the internet site. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

Processing system 28 can provide hemodynamic monitoring in more than one way.

In some embodiments, system 28 generates a separate output based on each of the signals as received by system 20. The output can include a graphical representation (e.g., as a function of the time) of the signals themselves, or their time-derivative (e.g., first time-derivative) or the area under the curves of the signals. Optionally and preferably system 28 performs a normalization procedure before generating the output, for example, to obtain similar scales for different output types.

In some embodiments, system 28 generates an output based on a combination of signals as received by system 20. Representative examples of such combinations are provided hereinbelow. When more than one combination is calculated by system 28 a separate output can optionally provided for each signal combination.

In some embodiments of the present invention system 28 applies a dynamically adaptive filter to the signal before displaying it. The filtration is preferably performed responsively to the physiological condition of the subject. The filtration can be done, for example, by employing the filtering techniques described in International Patent Publication No. 2009/022330 the contents of which are hereby incorporated by reference, separately to the phase and to the absolute components.

Generally, the dynamically variable filter filters the data according to a frequency band which is dynamically adapted in response to a change in the physiological condition of the subject. It was found by the Inventors of the present invention that the dynamical adaptation of the frequency band to the physiological condition of the subject can significantly reduce the influence of unrelated signals on the measured property.

Thus, in the present embodiment, system 28 employs a process in which first the physiological condition of the subject is determined, then a frequency band is selected based on the physiological condition of the subject, and thereafter the received signals are filtered according to frequency band. The frequency band is dynamically adapted in response to a change in the physiological condition.

The physiological condition is preferably, but not obligatorily, the heart rate of the subject. The data pertaining to the physiological condition can be collected via a suitable data collection unit either in analog or digital form, as desired. For example, the physiological condition can be a heart rate which can be determined, e.g., by analysis of ECG signals or the like.

While the embodiments below are described with a particular emphasis to physiological condition which is a heart rate, it is to be understood that more detailed reference to the heart rate is not to be interpreted as limiting the scope of the invention in any way. For example, in exemplary embodiments of the present invention the physiological condition is a ventilation rate of the subject, a repetition rate of a particular muscle unit and/or one or more characteristics of an action potential sensed electromyography.

The adaptation of the frequency band to the physiological condition can be according to any adaptation scheme known in the art. For example, one or more parameters of the frequency band (e.g., lower bound, upper bound, bandwidth, central frequency) can be a linear function of a parameter characterizing the physiological condition. Such parameter can be, for example, the number of heart beats per minute.

Figure 6A:
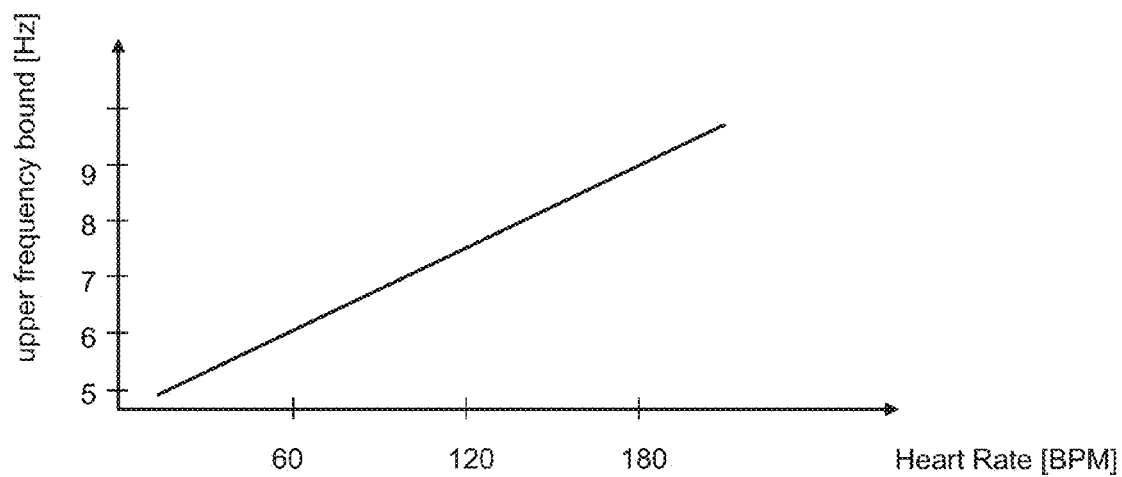
Figure 6B:
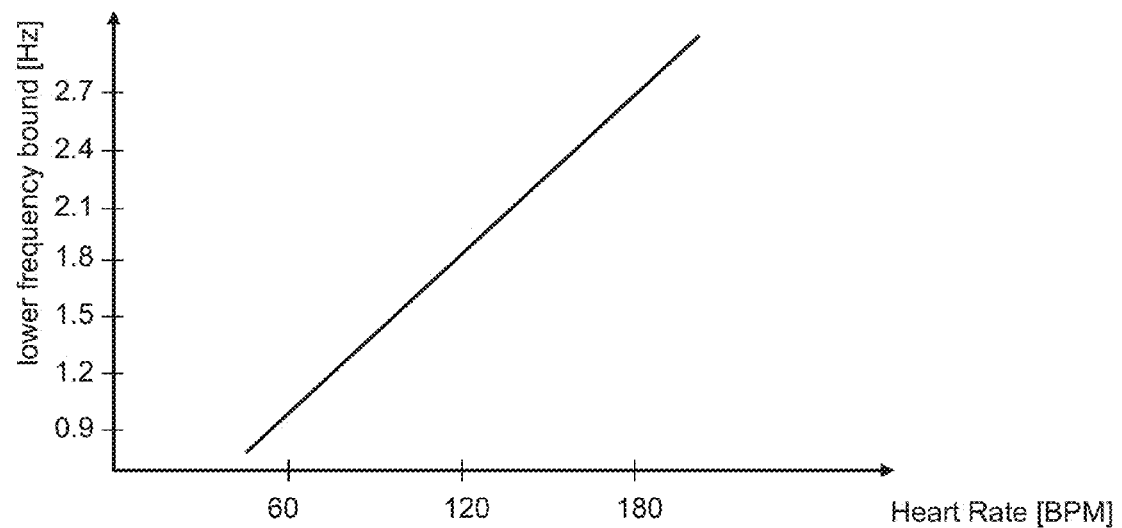

FIGS. 6A and 6B show representative examples of a dynamically varying frequency bounds, which can be employed according to some embodiments of the present invention separately to each signal received by system 28 and/or collectively to any combination of signals as further detailed hereinbelow.

Shown in FIGS. 6A and 6B is the functional dependence of the frequency bounds (upper bound in FIG. 6A and lower bound in FIG. 6B) on the heart rate of the subject. As shown in FIG. 6A, the upper bound of the frequency band varies linearly such that at a heart rate of about 60 beats per minute (bpm) the upper bound is about 6 Hz, and at a heart rate of about 180 bpm the upper bound is about 9 Hz. As shown in FIG. 6B, the lower bound of the frequency band varies linearly such that at a heart rate of about 60 the lower bound is about 0.9 Hz bpm and at a heart rate of about 180 bpm the lower bound is about 2.7 Hz.

In some embodiments of the present invention the upper bound approximately equals the function $F_U(HR)$ defined as $F_U(HR)=6+1.5\times[(HR/60)-1]$ Hz, where HR is the heart rate of the subject in units of bpm. In some embodiments, the upper bound equals $F_U(HR)$ at all times, while in other embodiments, the upper bound is set using an iterative process.

In some embodiments of the present invention the lower bound approximately equals the function $F_L(HR)$ defined as $F_L(HR)=0.9\times(HR/60)$ Hz. In some embodiments, the lower bound equals $F_L(HR)$ at all times while in other embodiments the lower bound is set by an iterative process.

Representative examples of iterative process suitable for some embodiments of the present invention are provided hereinunder.

Figure 6C:
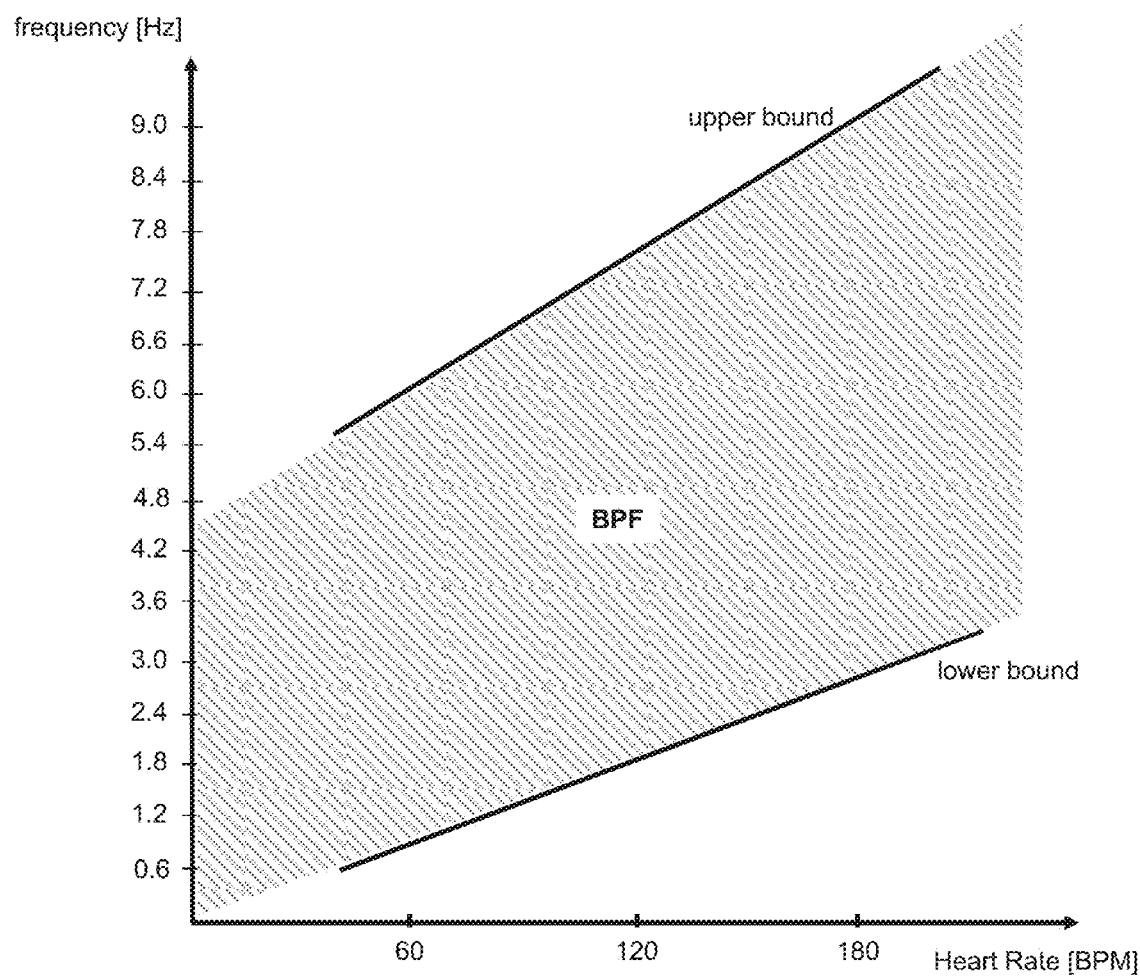

A dynamically varying band pass filter (BPF) characterized by a dynamically varying upper frequency bound and a dynamically varying lower frequency bound, according to some embodiments of the present invention is illustrated in FIG. 6C. As shown, each heart rate is associated with a frequency band defined by a lower bound and an upper bound. For example, for a heart rate of 60 bpm, FIG. 6C depicts a BPF in which the lower bound is about 0.9 Hz and the upper bound is about 6 Hz.

It is to be understood that the values presented above and the functional relations illustrated in FIGS. 6A-C are exemplary embodiments and should not be considered as limiting the scope of the present invention in any way. In other exemplary embodiments, the functional relations between the frequency band and the physiological condition can have different slopes and/or offsets, or they can be non-linear.

Following is a description of an iterative process for determining the frequency band of the band pass filter which filters to the phase component and separately the absolute component according to some embodiments of the present invention. The iterative process can, in some embodiments, be based a comparison between a value of a physiological parameter as extracted or calculated from the respective filtered component and a value of the same physiological parameter as extracted or calculated from a reference signal, for example, an ECG signal.

The term "physiological parameter" refers to any variable parameter which is measurable or calculable and is representative of a physiological activity, particularly, but not necessarily, activity of the heart. In various exemplary embodiments of the invention the physiological parameter is other than the heart rate per se. The physiological parameter can be a time-related parameter, amplitude-related parameters or combination thereof.

Typically, the filter signal and the reference signal are expressed in terms of amplitude as a function of the time. Thus, time-related parameters are typically calculated using abscissa values of the signals and amplitude-related parameters are is typically calculated using ordinate values of the signals.

Representative of time-related physiological parameters suitable for the present embodiments include, without limitation, systolic time, diastolic time, pre-ejection period and ejection time. A representative example of amplitude-related physiological parameter suitable for the present embodiments includes, without limitation, maximal amplitude above zero during a single beat, maximal peak-to-peak amplitude during a single beat, and RMS level during a single beat. Also contemplated are various slopes parameters, such as, but not limited to, the average slope between two points over the signal.

In various exemplary embodiments of the invention the physiological parameter is a ventricular ejection time (VET).

While the embodiments below are described with a particular emphasis to VET as the physiological parameter, it is to be understood that more detailed reference to VET is not to be interpreted as limiting the scope of the invention in any way.

The present inventors discovered that a significant amount of the biological information for a particular subject can be obtained from a frequency range between $F_L$(HR) and 5.5 Hz, where HR is the heart rate of the subject. It was further discovered by the present inventors that for some medical conditions some of the information can reside between 5.5 Hz and $F_U$(HR).

The advantage of the comparison between two different techniques for extracting or calculating the same physiological parameter, is that it allows to substantially optimize the upper frequency bound of the band pass filter. In various exemplary embodiments of the invention in each iteration of the iterative process, the comparison is repeated. If the comparison meets a predetermined criterion, the upper frequency bound is updated by calculating an average between a low threshold for the upper bound and a high threshold for the upper bound. The lower frequency bound can be a constant bound, e.g., a constant frequency which is from about 0.9 Hz to about 2.7 Hz), or it can be dynamic, e.g., $F_L$(HR), HR being the heart rate of the subject before or during the respective iteration.

The low and high thresholds for the upper bound can be set in more than one way. In some embodiments, the low and high thresholds are predetermined (namely they determined a priori before the iterative process), in some embodiments, the thresholds are set in a previous iteration of iterative process, in some embodiments one of the thresholds is predetermined and the other threshold is set in a previous iteration of iterative process. In any event, the first iteration is based on two thresholds which are determined a priori before the iterative process. It was found by the inventors of the present invention that, at least initially (i.e., at the first iteration), the first threshold can be about $F_U$(40), which in various exemplary embodiments of the invention is about 5.5 Hz, and the second threshold can be the calculated value of $F_U$(HR), HR being the heart rate of the subject before or during the respective iteration.

The predetermined criterion used during the iterations can be, for example, that the results of the two calculations are similar (e.g., within about 40% or 30% or 25% of each other). The predetermined criterion can also relate to the direction of difference between the two calculations. Broadly, for time-related parameters, the upper bound is updated if the value of the parameter as calculated based on the reference signal is higher than value of the parameter as calculated based on the filtered signal, and for amplitude-related parameters the upper bound is updated if the value of parameter as calculated based on the reference signal is lower than the value of the parameter as calculated based on the filtered signal. For slope-related parameters, the upper bound is typically updated if the value of the parameter as calculated based on the reference signal is higher than the value of the parameter as calculated based on the filtered signal.

A Boolean combination between the above criteria can also be used as a criterion. For example, an AND Boolean combination can be employed in which case the upper frequency bound can be updated if the results of the two calculations are similar and the calculation according to the filtered signal indicates an abnormal physiological condition while the calculation according to the reference signal indicates a normal physiological condition.

An iterative process for selecting the upper frequency bound, suitable for some exemplary embodiments of the present invention is described in International Patent Publication No. WO2010/032252, the contents of which are hereby incorporated by reference.

Following is a description of suitable signal combination which can be performed by processing system 28 according to some embodiments of the present invention. Each of the following signal combination can be used as a basis for generating an output indicative of the hemodynamics of organ 18, as further detailed hereinabove.

In some embodiments of the present invention processing system 28 combines input signals as obtained from each part of organ 18 (e.g., 36 and 38). The combination can be linear or non-linear combination. For example, denoting signal 36 by $S_R$ and signal 38 by $S_L$, system 28 can calculate a combined signal $S_{LR}$ using the following equation:

$$S_{LR} = w_L \times S_L^{\alpha L} + w_R \times S_R^{\alpha R} \quad (EQ. 5)$$

where $w_L$ and $w_R$ are predetermined weight parameters and $\alpha_L$ and $\alpha_R$ are predetermined power parameters. In some embodiment, $\alpha_L = \alpha_R = 1$, so that EQ. 5 expresses linear combination.

In some embodiments of the present invention processing system 28 combines the in-phase component with the quadrature component (e.g., components 24 and 26). For example, denoting signal 24 by I and signal 26 by Q, system 28 can calculate a hybrid signal $S_{IQ}$ using the following equation:

$$S_{IQ} = w_I \times S_I^{\alpha I} + w_Q \times S_Q \quad (EQ. 6)$$

where $w_I$ and $w_Q$ are predetermined weight parameters and $\alpha_I$ and $\alpha_Q$ are predetermined power parameters. In some embodiment, $\alpha_I = \alpha_Q = 1$, so that EQ. 6 expresses linear combination.

In some embodiments of the present invention processing system 28 combines, for each input signal, a respective in-phase component with a respective quadrature component. For example, for first input signal 36, system 28 can combine first in-phase component 40 with first quadrature component 42, and for second input signal 38, system 28 can combine second in-phase component 44 with second quadrature component 46.

Denoting components 40 and 42 by $Z_{iR}$ and $Z_{rR}$, respectively, system 28 can calculate a hybrid signal $S_{CR}$ using the following equation:

$$S_{CR} = w_{iR} \times Z_{iR}^{\alpha R} + w_{rR} \times Z_{rR}^{\beta R} \quad (EQ. 8)$$

where $w_{iR}$ and $w_{rR}$ are predetermined weight parameters and $\alpha_R$ and $\beta_R$ are predetermined power parameters. In some embodiment, $\alpha_R = \beta_R = 1$, so that EQ. 7 expresses linear combination.

Denoting components 44 and 46 by $Z_{iL}$ and $Z_{rL}$, respectively, system 28 can calculate a hybrid signal $S_{CL}$ using the following equation:

$$S_{CL} = w_{iL} \times Z_{iL}^{\alpha L} + w_{rL} \times Z_{rL}^{\beta L} \quad (EQ. 8)$$

where $w_{iL}$ and $w_{rL}$ are predetermined weight parameters and $\alpha_L$ and $\beta_L$ are predetermined power parameters. In some embodiment, $\alpha_L = \beta_L = 1$, so that EQ. 8 expresses linear combination.

In some embodiments of the present invention processing system 28 is configured to combine two or more hybrid signals. For example, system 28 can combine hybrid signals $S_{CR}$ and $S_{CL}$ to provide a combined hybrid signal $S_{CT}$, according to the following equation:

$$S_{CT} = w_{CR} \times S_{CR}^{\gamma R} + w_{CL} \times S_{CL}^{\gamma L} \quad (EQ. 9)$$

where $w_{CR}$ and $w_{CL}$ are predetermined weight parameters and $\gamma_L$ and $\gamma_L$ are predetermined power parameters. In some embodiment, $\gamma_L = \gamma_L = 1$, so that EQ. 9 expresses linear combination.

In some embodiments of the present invention processing system 28 combines the in-phase components of two or more input signals. For example, system 28 can combine the first in-phase component 40 with the second in-phase component 44. Using the above notations for components 40 and 44, system 28 can calculate a combined in-phase signal $S_{iT}$ using the following equation:

$$S_{iT} = w_{iR} \times Z_{iR}^{\alpha R} + w_{iL} \times Z_{iL}^{\alpha L}. \quad \text{(EQ. 10)}$$

As stated $\alpha_L$ and $\alpha_R$ can both be 1 so that EQ. 10 expresses linear combination.

In some embodiments of the present invention processing system 28 combines the quadrature components two or more input signals. For example, system 28 can combine first quadrature component 42 with second quadrature component 46, to provide a combined quadrature signal $S_{rT}$ using the following equation:

$$S_{rT} = w_{rR} \times Z_{rR}^{\alpha R} + w_{rL} \times Z_{rL}^{\alpha L}. \quad \text{(EQ. 11)}$$

When the power parameters satisfy $\alpha_L = \alpha_R = 1$ EQ. 11 expresses linear combination.

A combination of $S_{iT}$ and $S_{rT}$ is also contemplated. This combination is not explicitly formulated mathematically, but it can be obtained for example as described above with respect to EQ. 9.

In some embodiments of the present invention processing system 28 calculates, for each input signal, a phase component and an amplitude component. This can be done using EQ. 4 above and substituting the in-phase component for $Z_r$, and quadrature component for $Z_i$.

For example, the phase component $Z_{PMR}$ corresponding to the first input signal 36, the amplitude component $Z_{AMR}$ corresponding to the first input signal 36, the phase component $Z_{PML}$ corresponding to the second input signal 38, and the amplitude component $Z_{AML}$ corresponding to the second input signal 38 by $Z_{AMR}$, can be calculated as follows:

$$Z_{PMR} = \arctan(Z_{iR}/Z_{rR})$$

$$Z_{AMR} = \text{Sqrt}(Z_{rR}^2 + Z_{iR}^2)$$

$$Z_{PML} = \arctan(Z_{iL}/Z_{rL})$$

$$Z_{AML} = \text{sqrt}(Z_{rL}^2 + Z_{iL}^2) \quad \text{(EQ. 12)}$$

In some embodiments of the present invention processing system 28 calculates a combination of the phase component with amplitude component for each signal. For example, using EQ. 12, two phase-amplitude hybrid signals can be obtained:

$$S_{PL} = w_{AML} \times Z_{AML}^{\delta L} + w_{PML} \times Z_{PML}^{\epsilon L} \quad \text{(EQ. 13)}$$

$$S_{PR} = w_{AMR} \times Z_{AMR}^{\delta R} + w_{PMR} \times Z_{PMR}^{\epsilon R} \quad \text{(EQ. 14)}$$

where $w_{AML}$, $w_{PML}$, $w_{AMR}$ and $w_{PMR}$ are predetermined weight parameters and $\delta_L$, $\epsilon_L$, $\delta_R$, and $\epsilon_R$, are predetermined power parameters. When the power parameters satisfy $\delta_L = \epsilon_L = 1$ EQ. 13 expresses linear combination, and when the power parameters satisfy $\delta_R = \epsilon_R = 1$ EQ. 14 expresses linear combination.

In some embodiments of the present invention processing system 28 combines phase-amplitude hybrid signals corresponding to two or more input signals. For example, a combined phase-amplitude hybrid signal $Sp_T$ can be calculated as follows:

$$S_{PT} = w_{PR} \times S_{PR}^{\kappa R} + w_{PL} \times S_{PL}^{\kappa L} \quad \text{(EQ. 15)}$$

where $w_{PR}$ and $w_{PL}$ are predetermined weight parameters and $\kappa_L$ and $\kappa_L$ are predetermined power parameters. When the power parameters satisfy $\kappa_L = \kappa_L = 1$ EQ. 15 expresses linear combination.

Any of the weight parameters $w_L$, $w_R$, $w_I$, $w_Q$, $w_{iR}$, $w_{rR}$, $W_{iL}$, $w_{rL}$, $w_{CR}$, $w_{CL}$, $W_{iR}$, $W_{iL}$, $W_{rR}$, $W_{rL}$, $w_{AML}$, $w_{PML}$, $w_{AMR}$, $w_{PMR}$, $w_{PR}$ and $w_{PL}$; and any of the power parameters $\alpha_L$, $\alpha_R$, $\alpha_I$ $\alpha_Q$, $\beta_R$, $\beta_L$, $\gamma_R$, $\gamma_L$, $\delta_L$, $\epsilon_L$, $\delta_R$, $\epsilon_R$, $\kappa_R$ and $\kappa_L$, can be found prior to the monitoring for example, using a calibration curve. Typical values for the weight parameters, include, without limitation, any value from 0 to about 10, and typical values for the power parameters, include, without limitation any value from 0 to about 10.

In some embodiments, a normalization factor is employed. The normalization factor can be included in any of the signals of the present embodiments, including the signals listed in EQs. 5-15 or derivatives thereof or the area under their curves. A representative example of a normalization factor NF suitable for the present embodiments, includes, without limitation:

$$NF = W_{NF} \times Z_0^a \quad \text{(EQ. 16)}$$

where $Z_0$ is a baseline impedance either for each lead separately or for the entire organ, $W_{NF}$ is a weight parameter and a is a power parameter. The parameters $W_{NF}$ and a can be found, for example, using a calibration curve. Typical values for $W_{NF}$ parameter include, without limitation, any positive number up to about 5, and typical values for the power parameter a include, without limitation, any number from about −10 to 0.

In other embodiments, the normalization factor is calculated using the following relation:

$$NF = m \times \tan^2(\phi + c) + n \times \tan(\phi + d), \quad \text{(EQ. 17)}$$

where $\phi$ is the current phase in radians for each lead separately or for the entire organ, c and d are angle parameters, and m and n are multiplication parameters. The parameters c, d, m and n, can be found, for example, using a calibration curve. Typical values for the parameters c and d include, without limitation, any number from 0 to about 0.6 radians, and typical values for the parameters m and n include, without limitation, any number from −5 to about 5 radians.

For any of the signals of the present embodiments, including the signals listed in EQs. 5-15, a time-derivative, e.g., a first time derivative can be calculated. The time derivative can be calculated numerically. For example, denoting the time-dependence of an arbitrary signal by S(t), the first time derivative dS(t) can be calculated numerically as:

$$dS(t) = (S(t) - S(t - \Delta t))/\Delta t. \quad \text{(EQ. 18)}$$

Any of the signals of the present embodiments, for example, the signals listed in EQs. 5-15, including any time-derivative thereof, particularly a first time-derivative, can be used for assessing one or more properties pertaining to the hemodynamics of the organ. In some embodiments of the present invention the property is calculated based on at least one signal selected from the group consisting of the combined signal $S_{LR}$ (see, e.g., EQ. 5), the combined hybrid signal $S_{CT}$ (see, e.g., EQ. 9), and the combined phase-amplitude hybrid signal $S_{PT}$ (see, e.g., EQ. 15).

Once the properties are calculated, system 28 can generate an output based on the calculated properties or their time-derivative. The output can include a graphical representation, e.g., the calculated property as a function of the time.

For a given signal of the present embodiments, properties pertaining to the hemodynamics of the organ can be calculated using any technique known in the art, such as, but not limited to, the technique disclosed in International Publication Nos. WO2004/098376, WO2006/087696, WO2008/129535, WO2009/022330 and WO2010/032252 the contents of which are hereby incorporated by reference.

Representative examples of properties that can be calculated according to some embodiments of the present invention include, stroke volume (SV), cardiac output (CO), ventricular ejection time (VET), cardiac index (CI), thoracic fluid content (TFC), total peripheral resistance index (TPRI), blood vessel compliance and any combination thereof.

Figure 7:
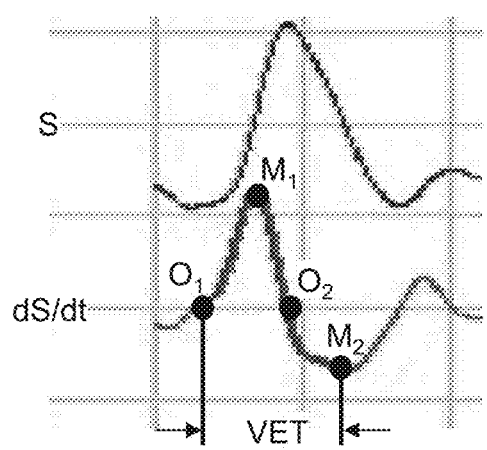

For example, the VET can be extracted from the morphology of the pulses of the signal being used for the calculation. In some embodiments of the present invention points of transitions are identified on the pulse and the time interval between two such points is defined as the VET. An exemplified procedure is illustrated in FIG. 7, which illustrates a typical morphology of a single beat of a signal S and its first derivative dS/dt, as a function of the time.

Signal S can be any of the signals of the present embodiments, e.g., $S_{LR}$ or $S_{CT}$ or $S_{PT}$, optionally and preferably following the application of a dynamically varying filter as further detailed hereinabove.

The derivative dS/dt has two zeroes $O_1$ and $O_2$ over the beat, with a point of local maximum $M_1$ between the zeroes and a point of local minimum $M_2$ after the second zero. In some embodiments of the present invention the VET is defined as the time period (difference between the abscissa values) between the first zero $O_1$ and the first minimum $M_2$ after the second zero $O_2$.

Other examples include the stroke volume SV and the cardiac output CO. The SV can be calculated based on dS/dt, a characteristic time-interval T and optionally one or more global characteristics of the subject such as, but not limited to, the weight, height, age, BMI and gender of the subject. In some embodiments of the present invention the time-interval is VET. SV can depend on dS/dt and T linearly, for example, $SV = c_{subject} \times T \times dS/dt$, where $c_{subject}$ is a constant which depends of one or more global characteristics of the subject. However, it is not intended to limit the scope of the present invention only to linear relation for calculating SV. Generally, SV is calculated according to the relation $SV = f(dS/dt, T, c_{subject})$ where $f$ is a function (not necessarily linear of dS/dt, T and $c_{subject}$. Alternatively, the function $f$ can be universal to all subjects, in which f does not vary with $c_{subject}$. In these embodiments, SV can be calculated according to the relation $SV = c_{subject} f(dS/dt, T)$ or $SV = f(dS/dt, T)$. A representative non-linear expression for the stroke volume SV include, without limitation:

$$SV = \left[ (w_1 \times (\text{Age})^{p1}) \times (w_2 \times (\text{Weight})^{p2}) \times \right. \quad \text{(EQ. 19)}$$
$$\left. (w_3 \times (\text{Height})^{p3}) \times \left( w_4 \times \left(\frac{dS}{dt}\right)^{p4} \right) \times (w_5 \times (VET)^{p5}) \right] \times w_6,$$

where Age is the age of the subject in years, Weight is the weight of the subject in Kg, Height is the height of the subject in cm, VET is the ventricular ejection time in ms, and dS/dt is the digital dimensionless representation of the first time derivative of the respective signal. The parameters $w_1, w_2, \ldots, w_6$ are weight parameters and the parameters $p_1, p_2, \ldots, p_5$ are power parameters.

The weight parameters $w_1, w_2, \ldots, w_6$ and power parameters $p_1, p_2, \ldots, p_5$, can be found, for example, using a calibration curve. Typical values for the weight parameters $w_1, w_2, \ldots, w_6$ include, without limitation, any number from about $10^{-10}$ to about $10^2$, and typical values for the power parameters $p_1, p_2, \ldots, p_5$ include, without limitation, any number from -2 to about 2.

The cardiac output CO can be calculated using the relation CO=SV×HR, where HR is the heart rate of the subject (e.g., in units of beats per minutes).

The calculated cardiac output can optionally and preferably be used for estimating the exercise capacity of the subject. Generally, the exercise capacity correlates with the cardiac output. For example, when the cardiac output is below a predetermined threshold, processing system 28 can estimate that the subject's exercise capacity is low, and when the cardiac output is above a predetermined threshold, the method can estimate that the subject's exercise capacity is high. It was demonstrated by the present inventors that during exercise the cardiac output among normal subjects is about 34% higher than that of Congestive Heart Failure (CHF) patients. The system of the present embodiments can therefore be used to assess or determine worsening of the condition of the subject, particularly subjects with congestive heart failure.

Optionally, a cardiopulmonary exercise testing is performed to provide one or more cardiopulmonary exercise (CPX) measures. The cardiac output can be combined with the CPX measure(s) and the combination can be used to estimate the exercise capacity, and/or to assess the quality of the estimation. For example, the maximal cardiac output is inversely correlated to the $VE/VCO_2$ slope, where VE is the ventilation efficiency and $VCO_2$ is the carbon dioxide production rate. The correlation coefficient between the maximal cardiac output during exercise and the $VE/VCO_2$ slope can be calculated and the quality of the exercise capacity estimation can be assessed based on this correlation coefficient, where negative and large in absolute value correlation coefficient corresponds to high quality of exercise capacity estimation and vice versa.

The maximal cardiac output is directly correlated to the oxygen uptake efficiency slope OUES. The correlation coefficient between the maximal cardiac output during exercise and the OUES can be calculated and the quality of the exercise capacity estimation can be assessed based on this correlation coefficient, where high positive correlation coefficient corresponds to high quality of exercise capacity estimation and vice versa.

The calculated cardiac output can optionally and preferably be used for identifying sleep apnea events. The present inventors conducted experiments in which cardiac output response to positive end expiratory pressure was evaluated. Without being bound to any theory, it is postulated that positive end expiratory pressure can be surrogate for sleep apnea because it creates positive thoracic pressure induced by mechanical ventilation in anesthetized subjects in intensive care units. The pressure dynamics in positive end expiratory pressure are similar to those observed during an apnea episode.

In various exemplary embodiments of the invention an apnea event is identified when the cardiac output is reduced by at least 30%, more preferably at least 40%, more preferably at least 50% over a time period of less than two minutes. In some embodiments, arterial oxygen saturation ($SPO_2$) is monitored, for example, conventional non-invasive pulse oximeter. In these embodiments a lower threshold of comprises reduction can be employed. For example, an apnea event can be identified when the calculated cardiac output is reduced by at least 25% and the value of $SPO_2$ is significantly decreased (say, by more than 40%).

Optionally, the hemoglobin concentration of the subject is estimated or received as input, and used for estimating blood oxygen content. The blood oxygen content can be supplemented to the calculated cardiac output for the purpose of improving sensitivity and/or specificity. In some embodiments of the present invention the total oxygen delivery is estimated. The total oxygen delivery can be estimated by combining the cardiac output, oxyhemoglobin saturation and hemoglobin concentration. For example, total oxygen delivery rate (typically expressed in units of mL of oxygen per minute) can be estimated by multiplying the cardiac output by the oxygen content.

When the total oxygen delivery falls below a predetermined threshold which can be expressed as percentage of baselines, system 10 can generate a wakening alarm sensible by the sleeping subject.

The present embodiments can also be employed for subjects who already been diagnosed with sleep apnea and for whom a CPAP device has been prescribed. Specifically, the present embodiments can be used as a supplement to a conventional treatment (e.g., a CPAP device) so as to assess the efficacy of treatment. For example, the present embodiments can be used for determining whether or not a sufficient amount of oxygen is delivered to vital organs such as the brain, heart and kidneys. It is recognized that even when a CPAP device pushes air to the lungs, oxygen delivery from the cardio-pulmonary system to vital tissues is not guaranteed. For example, a significant drop in cardiac output may result in insufficient oxygen delivery even when the CPAP device increases the oxygen content in the blood. In this case, a system according to some embodiments of the present invention can signal the CPAP device to increase the positive airway pressure and/or generate a wakening signal sensible by the sleeping subject. Thus, according to some embodiments of the present invention when the total oxygen delivery falls below the predetermined threshold system 10 can control a CPAP device to increase pressure.

The calculated property can also be used for predicting onset of electromechanical dissociation. It was found by the present inventors that the onset of electromechanical dissociation can be predicted ahead of time, unlike traditional techniques which only provide post occurrence identification of electromechanical dissociation. The present embodiments predict electromechanical dissociation onset by providing a quantitative estimate of the mechanical activity of the heart while monitoring its electrical activity. Specifically, according to the present embodiments onset of electromechanical dissociation is likely to occur, if the flow rate characterizing the mechanical activity of the heart is lower than one predetermined threshold while the rhythm characterizing the electrical activity of the heart remains above another predetermined threshold.

Thus, in various exemplary embodiments of the invention an electrocardiac signal e.g., electrocardiogram (ECG) signal or a signal which correlates with an ECG signal is obtained. The electrocardiac signal can be obtained from an external source, or be extracted from the signal of the present embodiments. Typically, the electrocardiac signal comprises a DC signal or a signal characterized by very low frequency (less than 150 Hz). ECG signals, for example, are typically characterized by amplitudes of 0.1-5 mV and frequencies of 0.05-130 Hz.

The extraction of DC signal or a very low frequency signal can be done using a suitable electronic circuitry or device which receives the signal of the present embodiments and filter out high frequency (typically radiofrequency) components. Such electronic circuitries are known in the art. For example, a feedback capacitor or an integrator type electronic circuitry can be constituted to extract the electrocardiac signal. Optionally, the electronic circuitry can amplify the electrocardiac signal as known in the art.

The electrical activity of the heart can be assessed based on the electrocardiac signal. Preferably, but not obligatorily one or more repetitive patterns are identified in the electrocardiac signal, and the repetition rate of the identified patterns is measured. For example, when the electrocardiac signal is an ECG signal, the QRS complex can be identified, and the QRS rate can be measured, for example, by measuring the RR interval and defining the rate as the inverse of the RR interval.

The mechanical activity of the heart can be assessed based on the calculated property, preferably, but not necessarily the cardiac output or cardiac index or stroke volume.

Once the electrical and mechanical activities are assessed, processing system 28 predicts the onset of electromechanical dissociation (EMD) or Pulseless Electrical Activity (PEA) according to predetermined criteria. Generally, when the electrical activity is above a predetermined threshold and the mechanical activity is below a predetermined threshold, processing system 28 predicts onset of EMD or PEA.

For example, when the calculated property is cardiac output the predetermined threshold for the mechanical activity can be about X liters per minute, where X is a number ranging from about 1 to about 1.5. Alternatively, a baseline cardiac output for the subject can be defined and compared to the instantaneous cardiac output. In this embodiment, the predetermined threshold for the mechanical activity can be defined as 70% or 60% or 50% of the baseline.

When the calculated property is cardiac index (cardiac output per unit surface area of the subject's body) the predetermined threshold for the mechanical activity can be about Y liters per minute per square meter, where Y is a number ranging from about 0.75 to about 1. Alternatively, a baseline cardiac index for the subject can be defined and compared to the instantaneous cardiac index, wherein the predetermined threshold for the mechanical activity can be defined as 70% or 60% or 50% of the baseline.

Following are some representative for criteria suitable for predicting EMD. The onset of EMD can be predicted if the cardiac output is reduced by at least 50% and the electrical activity is characterized by pulse rate of at least 60 pulses per minute. The onset of EMD can also be predicted if, over a period of about five minutes, the cardiac output is less than 1 liter per minute and the electrical activity is characterized by a rhythm of at least 40 cycles per minute. The onset of EMD can also be predicted if, over a period of about five minutes, the cardiac index is less than 1 liter per minute per square meter and the electrical activity is characterized by a rhythm of at least 40 cycles per minute. The onset of EMD can be predicted if, over a period of about five minutes, the cardiac index is less than 0.75 liter per minute per square meter and the electrical activity is characterized by a rhythm of at least 40 cycles per minute.

The morphology of the signal of the present embodiments can be used according to some embodiments of the present invention to calculate the likelihood that the subject develops sepsis.

In various exemplary embodiments of the invention a sepsis indicator is extracted from the pulse morphology, and the likelihood is assessed based on the sepsis indicator. The assessment can be done, for example, by thresholding, wherein the sepsis indicator as obtained from the pulse morphology is compared to a predetermined threshold which can be used as a criterion to assess whether or not the subject is likely to develop sepsis.

In some embodiments of the present invention the sepsis indicator is a ratio between the time-derivative of the obtained signal (e.g., $S_{LR}$ or $S_{CT}$ or $S_{PT}$) and the ventricular ejection time.

Without wishing to be bound by any particular theory, the present inventors identified that this ratio reflects the relative behavior of contractility per time to eject. Thus, this ratio also reflects the cardiac work against the after load pressures. In cases of hyperdynamic cardiac performance, such as septic shock and liver failure or cirrhosis, the heart contracts in relatively enhanced contractile force against a low after load. This results in a higher value of the ratio. Thus, such a ratio can be used according to some embodiments of the present invention for assessing the likelihood for the subject to develop sepsis. The present inventors conducted experiments and uncovered that this ratio can be used as a discriminator for screening septic and non-septic subjects. It was found that for septic subjects, this ratio is generally high, wherein for non-septic subjects this ratio is generally low.

When the above ratio is used as a sepsis indicator, the ratio is optionally and preferably compared to a predetermined threshold, wherein a ratio above the predetermined threshold indicates that the subject is likely to develop sepsis, and a ratio above the predetermined threshold indicates that the subject is not likely to develop sepsis. Typical values for the predetermined threshold are from about 0.5 to about 0.8, or from about 0.6 to about 0.8, e.g., about 0.7. It was found by the present inventors that using such threshold, the likelihood is characterized by a p-value less than 0.1, e.g., 0.05.

Optionally and preferably a report is issued. The report can include the assessed likelihood and optionally other parameters, particularly statistical parameters (e.g., characteristic p-value and the like).

The signals of the present embodiments can also be used for other applications including, without limitation, predicting body cell mass, fat free mass and/or total body water of a subject, for example, as disclosed in U.S. Pat. No. 5,615,689, the contents of which are hereby incorporated by reference; determining hematocrit of blood in a body part of a subject, for example, as disclosed in U.S. Pat. No. 5,642,734, the contents of which are hereby incorporated by reference; monitoring hydration status of a subject, for example, as disclosed in U.S. Published Application No. 20030120170, the contents of which are hereby incorporated by reference; discriminating tissue, for example, as disclosed in U.S. Published Application No. 20060085048, the contents of which are hereby incorporated by reference; and calculating the circumference of a body segment for example, as disclosed in U.S. Published Application No. 20060122540, the contents of which are hereby incorporated by reference.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Prototype System

Figure 8:
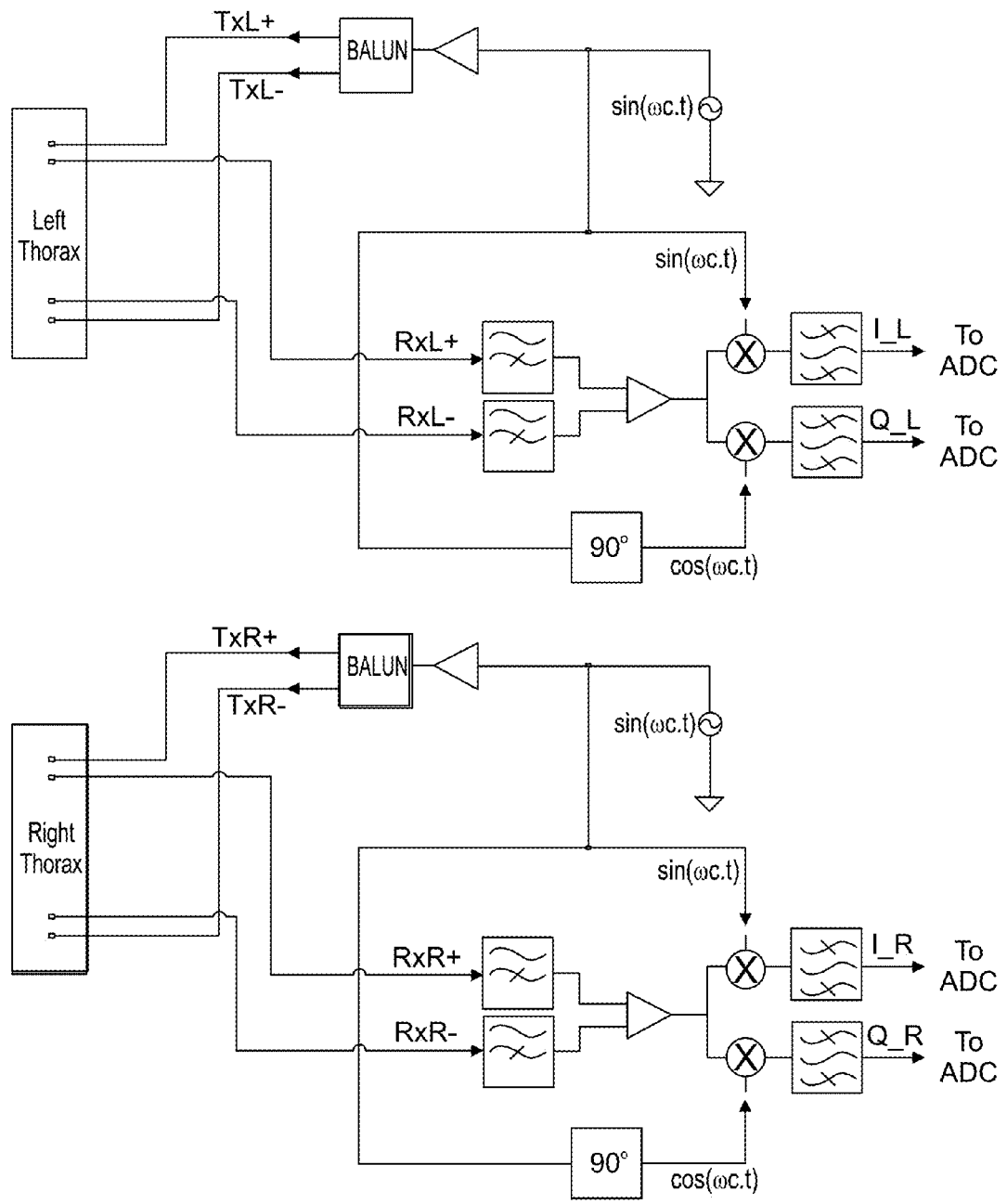

A prototype system was built according to some embodiments of the present invention. The system included circuitry for generating and transmitting the output signals are receiving and demodulating the input signals. The circuitry is illustrated in FIG. 8.

The prototype system included left and right lead transmitters and two I/Q detectors for the detection of the thoracic impedance. Transmitted low current sinusoidal signals from a current source were transmitted, via balun circuits, separately to a left lead and a right lead ($T_{xL}$ and $T_{xR}$). The signals were transmitted to the thorax via dedicated transmitting electrodes that were attached to the skin.

The received modulated signals from each lead ($R_{xL}$ and $R_{xR}$) were filtered using a high pass filter having a cutoff frequency of about 50 Hz, and thereafter multiplied, in parallel, by (i) $T_{xL}$ and $T_{xR}$, respectively, and (ii) $T_{xL}$ and $T_{xR}$ after they were shifted by $\pi/2$. The two resulting multiplication signals from each lead underwent a band pass filter with upper cutoff selected to obtained the in-phase and quadrature signals and low cutoff for eliminating respiratory, resulting in a left and right in-phase components (I_L, I_R, respectively) and a left and right quadrature components (Q_L, Q_R, respectively). The lower and upper cutoff frequencies of the band pass filter were 0.8 Hz and 9 Hz, respectively. These four signals were then sampled at a sampling rate of 500 Hz by Analog to Digital Convertors for further processing in the digital processor (not shown).

Animal Study

Two pigs weighing 55 Kg and two Beagle dogs weighing 9 Kg where used for the experiment.

For the pigs, an ultrasonic flow probe was adjusted to the ascending Aorta and for the dogs a Electromagnetic flow probe was adjusted to the ascending Aorta both devices are considered Gold Standard in measuring the flow from the Left Ventricle to the aorta.

In addition, A Fr. micromanometer was inserted into the left ventricle via a stab in the apex and secured with a purse string suture for the measurement of pressure and volume within the left ventricle.

Four sensors were placed around the thorax for the detection of the different thoracic impedance based signal of the present embodiments. After the experimental setup, various pharmaceutical and surgical interventions were employed with the goal of creating acute, large hemodynamic variations which would be used to test the behavior of the system as compared with the invasive gold-standard.

The following Interventions were performed:
(i) Baseline steady-state hemodynamic data was recorded for 10 minutes.
(ii) Infusion of intravenous fluid—500 cc/200 cc of normal saline (pigs/dogs respectively) was infused over 10 minutes to increase blood volume and CO.
(iii) PEEP Test: The positive end expiratory pressure (PEEP) was increased to between 10 to 15 cmH$_2$O in order to reduce CO. PEEP testing is a recognized method to create acute reductions in CO, where the physiological mechanism works by reducing venous blood flow returning to the heart by creating a more positive pressure environment in the thorax.
(iv) Dobutamine infusion for pigs and Phenilephrine infusion for dogs—a rapid onset, short-acting cardiac stimulant, Dobutamine/Phenilephrine progressively increases CO, generally to a level twice that present prior to drug administration; infusion was stopped after 5-10 minutes.
(v) Esmolol injection—a fast onset, short duration beta-blocker, esmolol reverses the effects of Dobutamine/Phenilephrine, rapidly decreasing CO.
(vi) Oleic Acid Infusion—Oleic Acid was infused during 60 minutes to produce Pulmonary Edema resulting in declining blood flow and right Heart Insufficiency.
(vii) Sacrifice and tissue harvest—saturated potassium chloride was injected into the heart to cause instant cardiac arrest; any offset in the aortic flow values were recorded.

Results

Figure 9A:
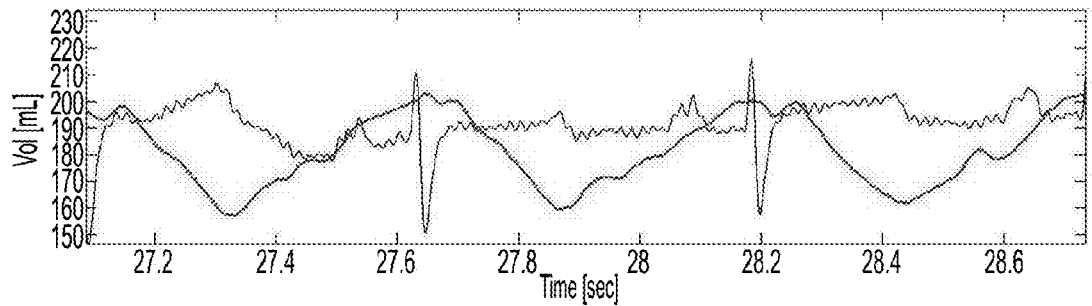

FIG. 9A shows the left ventricle volume signal in ml as derived by the Micromanometer (blue) synchronized with the ECG signal (black), as a function of time in seconds. The ECG is scaled for display purposes.

Figure 9B:
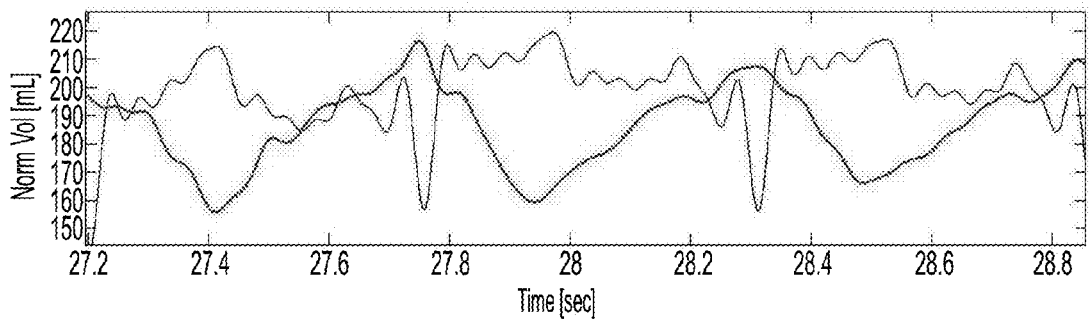

FIG. 9B shows the signal $S_{CT}(t)$ in ml (red) synchronized with the ECG signal in black. Both the $S_{CT}$ signal and the ECG signal are scaled for display purposes.

FIGS. 9A-B demonstrate that the signal $S_{CT}(t)$ of the present embodiments correlates well with the volume of blood in the ventricles of the heart.

FIG. 10 shows the left ventricle flow signal as derived by the ultrasonic flow probe (blue), synchronized with the ECG signal (red), as a function of time in seconds.

FIG. 10 also shows the $dS_{CT}(t)$ signal of the present embodiments (black). Both the $dS_{CT}$ signal and the ECG signal are scaled for display purposes.

FIG. 10 demonstrates that the area under the positive curve of the signal $dS_{CT}(t)$ correlates well with the flow of blood from the left ventricle to the aorta.

FIG. 11 shows the mean cardiac output in liters/minute as derived by the aortic ultrasonic flow probe (blue), and the mean cardiac output derived by the $dS_{CT}(t)$ signal of the present embodiments (red), during infusion of Dobutamine, as a function of the time in seconds.

FIG. 11 demonstrates that the signal $dS_{CT}(t)$ of the present embodiments correlates with high precision the hemodynamic behavior.

FIG. 12A shows, as a function of the number of heart beat, the mean cardiac output in liters/minute as derived by the aortic ultrasonic flow probe (blue), and the mean cardiac output in liters/minute derived by the signal $dS_{CL}(t)$ of the present embodiments (black), after the infusion of Dobutamine was ended. The signal $dS_{CL}(t)$ is scaled.

FIG. 12B shows, as a function of the number of heart beat, the mean cardiac output in liters/minute (blue) as derived by the aortic ultrasonic flow probe, and the mean cardiac output in liters/minute as derived by the signal $dS_{CR}(t)$ of the present embodiments (black). The signal $dS_{CR}(t)$ is scaled and is presented at the same time frame as in FIG. 12A. The left lead showed more correlation with the reference compared to the right lead.

FIG. 13A shows, as a function of the number of heart beat, the mean cardiac output in liters/minute derived by an aortic ultrasonic flow probe (blue), and the mean cardiac output in liters/minute as derived by the signal $dS_{CR}(t)$ of the present embodiments (black), during progression of Severe Edema. The signal $dS_{CR}(t)$ is scaled.

FIG. 13B shows, as a function of the number of heart beat, the mean cardiac output in liters/minute as derived by an aortic ultrasonic flow probe (blue), and the mean cardiac output in liters/minute as derived by the signal $dS_{CL}(t)$ of the present embodiments (black). The signal $dS_{CL}(t)$ is scaled and is presented at the same time frame as in FIG. 13A. The right lead showed more correlation with the reference compared to the left lead.

The present example demonstrates that the hemodynamic trends invoked by drug titration and captured with the experimental system of the present embodiments correlated well with the Gold Standard in $S_{CL}(t)$ (see FIGS. 12A-B) and hemodynamic trends invoked by fluid challenge or respiratory challenged were described in high correlation in $S_{CR}(t)$ (see FIGS. 13A-B).

These finding can be explained by the physiologic response wherein the volume and respiration challenges impact firstly the right heart, before blood flow continues to the left circulation after passing the pulmonary circulation. On the other hand, vasoactive drugs impact the peripheral arterial circulation or the heart itself, are first manifested in left heart output.

FIG. 14 shows, as a function of the number of heart beat, the mean cardiac output in liters/minute as derived by an aortic ultrasonic flow probe (blue), and mean cardiac output in liters/minute derived by the signal $dS_{PT}(t)$ of the present embodiments (black), during infusion of 500 cc fluid bolus. The signal $dS_{PT}(t)$ is scaled. FIG. 14 demonstrates that the signal $Sp_T(t)$ correlates with the cardiac output of the reference.

REFERENCES

[1] Rich et al., Noninvasive Cardiac Output in Pulmonary Hypertension
[2] Rich et al., Evaluation Of Noninvasively Measured Cardiac Output In Patients With Pulmonary Hypertension
[3] Marque et al., Comparison between Flotrac-Vigileo and Bioreactance, a totally noninvasive method for cardiac output monitoring, Critical Care Vol 13 No 3
[4] Heerdt et al., Noninvasive cardiac output monitoring with bioreactance as an alternative to invasive instrumentation for preclinical drug evaluation in beagles, Journal of Pharmacological and Toxicological Methods
[5] Raval, et al., Multicenter Evaluation Of Noninvasive Cardiac Output Measurement By Bioreactance Technique, Journal of Clinical Monitoring and Computing
[6] Squara et al., Comparison of monitoring performance of Bioreactance vs. pulse contour during lung recruitment maneuvers, Critical Care 2009, 13:R125
[7] Squara et al., Noninvasive cardiac output monitoring (NICOM): a clinical validation, Intensive Care Med.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A system for monitoring hemodynamics of a subject, comprising:
   a signal generating system configured for providing at least an output electric signal and transmitting said output signal to an organ of the subject;
   a demodulation system configured for receiving an input electrical signal sensed from the organ responsively to said output electric signal, and for modulating said input signal using said output signal to provide an in-phase component and a quadrature component of said input signal;
   a processing system configured combine said in-phase component with said quadrature component thereby to generate a hybrid signal, and for monitoring the hemodynamics based at least in part on said hybrid signal wherein said hybrid signal comprises a linear combination of said components.

2. The system according to claim 1, wherein said signal generating system is configured for providing a first output electric signal and a second output electric signal, and transmitting each of said output signals to a separate part of the organ; and
   wherein said demodulation system is configured for receiving an input electrical signal sensed from each part of the organ responsively to a respective output electric signal, and for modulating signals to provide an in-phase component and a quadrature component of each of said input signals.

3. The system according to claim 2, wherein said first and said second output electric signals are dependent electrical signals.

4. The system according to claim 2, wherein said first and said second output electric signals are independent electrical signals.

5. The system according to claim 2, wherein said processing system is configured to combine, for each input signal, a respective in-phase component with a respective quadrature component thereby to generate a hybrid signal corresponding to said input signal, and wherein said monitoring is based at least in part on said hybrid signals.

6. The system according to claim 5, wherein said processing system is configured to combine said hybrid signals, thereby to provide a combined hybrid signal, and wherein said monitoring is based at least in part on said combined hybrid signals.

7. The system according to claim 6, wherein said processing system is configured to asses, based on said combined hybrid signal, at least one property selected from the group consisting of stroke volume (SV), cardiac output (CO), ventricular ejection time (VET), cardiac index (CI), thoracic fluid content (TFC), total peripheral resistance index (TPRI), blood vessel compliance, oxygen uptake efficiency slope (OUES), and a derivative of a phase component of said input signal.

8. The system according to claim 6, wherein said processing system is configured to estimate exercise capacity of the subject based on said combined hybrid signal.

9. The system according to claim 6, wherein said processing system is configured to identify sleep apnea events based on said combined hybrid signal.

10. The system according to claim 6, wherein said processing system is configured to assess the likelihood that the subject develops sepsis based on said combined hybrid signal.

11. The system according to claim 6, wherein said processing system is configured to predict onset of electromechanical dissociation based on said combined hybrid signal.

12. The system according to claim 6, wherein said processing system is configured to assess blood hematocrit based on said combined hybrid signal.

13. The system according to claim 2, wherein said processing system is configured to combine an in-phase component of a first input signal with an in-phase component of a second input signal to provide a combined in-phase signal, and wherein said monitoring is based at least in part on said combined in-phase signal.

14. The system according to claim 2, wherein said processing system is configured to combine a quadrature component of a first input signal with a quadrature component of a second input signal to provide a combined quadrature signal, and wherein said monitoring is based at least in part on said combined quadrature signal.

15. The system according to claim 2, wherein said processing system is configured to calculate, for each input signal, a phase component, an amplitude component, and a phase-amplitude hybrid signal defined as a combination of phase component with amplitude component, and wherein said monitoring is based at least in part on said combination.

16. The system according to claim 15, wherein said processing system is configured to combine a phase-amplitude hybrid signal corresponding to said first input signal with a phase-amplitude hybrid signal corresponding to said second input signal, thereby to provide a combined phase-amplitude hybrid signal and wherein said monitoring is based at least in part on said combined phase-amplitude hybrid signal.

17. The system according to claim 16, wherein said processing system is configured to assess, based on said combined phase-amplitude hybrid signal, at least one property selected from the group consisting of stroke volume (SV), cardiac output (CO), ventricular ejection time (VET), cardiac index (CI), thoracic fluid content (TFC), total peripheral resistance index (TPRI), blood vessel compliance, oxygen uptake efficiency slope (OUES), and a derivative of a phase component of said input signal.

18. A method of monitoring hemodynamics of a subject, comprising:
    generating at least an output electric signal and transmitting said output signal to an organ of the subject;
    sensing an input electrical signal from the organ responsively to said output electric signal;
    modulating said input signal using said output signal to provide an in-phase component and a quadrature component of said input signal;
    combining said in-phase component with said quadrature component to generate a hybrid signal; and
    monitoring the hemodynamics based at least in part on said hybrid signal;
    wherein said hybrid signal comprises a linear combination of said components.

19. The method according to claim 18, wherein said generating and said transmitting comprises providing a first output electric signal and a second output electric signal, and transmitting each of said output signals to a separate part of the organ;
    wherein said sensing comprises sensing an input electrical signal from each part of the organ responsively to a respective output electric signal; and
    wherein said modulating comprise modulating each input signal to provide an in-phase component and a quadrature component of said input signal.

20. The method according to claim 19, further comprising combining, for each input signal, a respective in-phase component with a respective quadrature component to generate a hybrid signal corresponding to said input signal, wherein said monitoring is based at least in part on said hybrid signals.

21. The method according to claim 20, further comprising combining said hybrid signals to provide a combined hybrid signal, wherein said monitoring is based at least in part on said combined hybrid signals.

22. The method according to claim 19, further comprising combining an in-phase component of a first input signal with an in-phase component of a second input signal to provide a combined in-phase signal, wherein said monitoring is based at least in part on said combined in-phase signal.

23. The method according to claim 19, further comprising combining a quadrature component of a first input signal with a quadrature component of a second input signal to provide a combined quadrature signal, wherein said monitoring is based at least in part on said combined quadrature signal.

24. The method according to claim 19, further comprising calculating, for each input signal, a phase component, an amplitude component, and a phase-amplitude hybrid signal defined as a combination of phase component with amplitude component, wherein said monitoring is based at least in part on said combination.

25. The method according to claim 24, further comprising combining a phase-amplitude hybrid signal corresponding to said first input signal with a phase-amplitude hybrid signal corresponding to said second input signal to provide a combined phase-amplitude hybrid signal, wherein said monitoring is based at least in part on said combined phase-amplitude hybrid signal.

26. A system for monitoring hemodynamics of a subject, comprising:
    a signal generating system configured for providing at least an output electric signal and transmitting said output signal to an organ of the subject;
    a demodulation system configured for receiving an input electrical signal sensed from the organ responsively to said output electric signal, and for modulating said input signal using said output signal to provide an in-phase component and a quadrature component of said input signal;
    a processing system configured combine said in-phase component with said quadrature component thereby to generate a hybrid signal, and for monitoring the hemodynamics based at least in part on said hybrid signal wherein said hybrid signal comprises a non-linear combination of said components.

27. The system according to claim 26, wherein said signal generating system is configured for providing a first output electric signal and a second output electric signal, and transmitting each of said output signals to a separate part of the organ; and
    wherein said demodulation system is configured for receiving an input electrical signal sensed from each part of the organ responsively to a respective output electric signal, and for modulating signals to provide an in-phase component and a quadrature component of each of said input signals.

28. The system according to claim 27, wherein said first and said second output electric signals are dependent electrical signals.

29. The system according to claim 27, wherein said first and said second output electric signals are independent electrical signals.

30. The system according to claim 27, wherein said processing system is configured to combine, for each input signal, a respective in-phase component with a respective quadrature component thereby to generate a hybrid signal corresponding to said input signal, and wherein said monitoring is based at least in part on said hybrid signals.

31. The system according to claim 30, wherein said processing system is configured to combine said hybrid signals, thereby to provide a combined hybrid signal, and wherein said monitoring is based at least in part on said combined hybrid signals.

32. The system according to claim 31, wherein said processing system is configured to perform, based on said combined hybrid signal, at least one operation selected from the group consisting of:
    (i) assessing at least one property selected from the group consisting of stroke volume (SV), cardiac output (CO), ventricular ejection time (VET), cardiac index (CI), thoracic fluid content (TFC), total peripheral resistance index (TPRI), blood vessel compliance, oxygen uptake efficiency slope (OUES), and a derivative of a phase component of said input signal;
(ii) estimating exercise capacity of the subject;
(iii) identifying sleep apnea events;
(iv) assessing the likelihood that the subject develops sepsis;
(v) predicting onset of electromechanical dissociation; and
(vi) assessing blood hematocrit.

33. The system according to claim 27, wherein said processing system is configured to combine an in-phase component of a first input signal with an in-phase component of a second input signal to provide a combined in-phase signal, and wherein said monitoring is based at least in part on said combined in-phase signal.

34. The system according to claim 27, wherein said processing system is configured to combine a quadrature component of a first input signal with a quadrature component of a second input signal to provide a combined quadrature signal, and wherein said monitoring is based at least in part on said combined quadrature signal.

35. The system according to claim 27, wherein said processing system is configured to calculate, for each input signal, a phase component, an amplitude component, and a phase-amplitude hybrid signal defined as a combination of phase component with amplitude component, and wherein said monitoring is based at least in part on said combination.

36. The system according to claim 35, wherein said processing system is configured to combine a phase-amplitude hybrid signal corresponding to said first input signal with a phase-amplitude hybrid signal corresponding to said second input signal, thereby to provide a combined phase-amplitude hybrid signal and wherein said monitoring is based at least in part on said combined phase-amplitude hybrid signal.

37. The system according to claim 36, wherein said processing system is configured to assess, based on said combined phase-amplitude hybrid signal, at least one property selected from the group consisting of stroke volume (SV), cardiac output (CO), ventricular ejection time (VET), cardiac index (CI), thoracic fluid content (TFC), total peripheral resistance index (TPRI), blood vessel compliance, oxygen uptake efficiency slope (OUES), and a derivative of a phase component of said input signal.

38. A system for monitoring hemodynamics of a subject, comprising:
a signal generating system configured for providing a first output electric signal and a second output electric signal, and transmitting each of said output signals to a separate part of the organ;
a demodulation system configured for receiving an input electrical signal sensed from each part of the organ responsively to a respective output electric signal, and for modulating signals to provide an in-phase component and a quadrature component of each of said input signals; and
a processing system configured to combine, for each input signal, a respective in-phase component with a respective quadrature component thereby to generate a hybrid signal corresponding to said input signal, and wherein said monitoring is based at least in part on said hybrid signals, to combine said hybrid signals, thereby to provide a combined hybrid signal, to monitor the hemodynamics based at least in part on said combined hybrid signals, and to identify sleep apnea events based on said combined hybrid signal.

39. The system according to claim 38, wherein said first and said second output electric signals are dependent electrical signals.

40. The system according to claim 38, wherein said first and said second output electric signals are independent electrical signals.

41. The system according to claim 38, wherein said processing system is configured to asses, based on said combined hybrid signal, at least one property selected from the group consisting of stroke volume (SV), cardiac output (CO), ventricular ejection time (VET), cardiac index (CI), thoracic fluid content (TFC), total peripheral resistance index (TPRI), blood vessel compliance, oxygen uptake efficiency slope (OUES), and a derivative of a phase component of said input signal.

42. The system according to claim 38, wherein said processing system is configured to estimate exercise capacity of the subject based on said combined hybrid signal.

43. The system according to claim 38, wherein said processing system is configured to assess the likelihood that the subject develops sepsis based on said combined hybrid signal.

44. The system according to claim 38, wherein said processing system is configured to predict onset of electromechanical dissociation based on said combined hybrid signal.

45. The system according to claim 38, wherein said processing system is configured to assess blood hematocrit based on said combined hybrid signal.

46. A method of monitoring hemodynamics of a subject, comprising:
generating at least an output electric signal and transmitting said output signal to an organ of the subject;
sensing an input electrical signal from the organ responsively to said output electric signal;
modulating said input signal using said output signal to provide an in-phase component and a quadrature component of said input signal;
combining said in-phase component with said quadrature component to generate a hybrid signal; and
monitoring the hemodynamics based at least in part on said hybrid signal;
wherein said hybrid signal comprises a non-linear combination of said components.

47. The method according to claim 46, wherein said generating and said transmitting comprises providing a first output electric signal and a second output electric signal, and transmitting each of said output signals to a separate part of the organ;
wherein said sensing comprises sensing an input electrical signal from each part of the organ responsively to a respective output electric signal; and
wherein said modulating comprise modulating each input signal to provide an in-phase component and a quadrature component of said input signal.

48. The method according to claim 47, further comprising combining, for each input signal, a respective in-phase component with a respective quadrature component to generate a hybrid signal corresponding to said input signal, wherein said monitoring is based at least in part on said hybrid signals.

49. The method according to claim 48, further comprising combining said hybrid signals to provide a combined hybrid signal, wherein said monitoring is based at least in part on said combined hybrid signals.

50. The method according to claim 47, further comprising combining an in-phase component of a first input signal with an in-phase component of a second input signal to provide a combined in-phase signal, wherein said monitoring is based at least in part on said combined in-phase signal.

51. The method according to claim 47, further comprising combining a quadrature component of a first input signal with a quadrature component of a second input signal to provide a combined quadrature signal, wherein said monitoring is based at least in part on said combined quadrature signal.

52. The method according to claim 47, further comprising calculating, for each input signal, a phase component, an amplitude component, and a phase-amplitude hybrid signal defined as a combination of phase component with amplitude component, wherein said monitoring is based at least in part on said combination.

53. The method according to claim 52, further comprising combining a phase-amplitude hybrid signal corresponding to said first input signal with a phase-amplitude hybrid signal corresponding to said second input signal to provide a combined phase-amplitude hybrid signal, wherein said monitoring is based at least in part on said combined phase-amplitude hybrid signal.

* * * * *